United States Patent
Druma et al.

(10) Patent No.: US 10,993,755 B2
(45) Date of Patent: May 4, 2021

(54) INFLATABLE BONE TAMP WITH FLOW CONTROL AND METHODS OF USE

(71) Applicant: MEDTRONIC HOLDING COMPANY SÀRL, Tolochenaz (CH)

(72) Inventors: Calin Druma, San Jose, CA (US); Shankar Kar, Santa Clara, CA (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 199 days.

(21) Appl. No.: 16/353,412

(22) Filed: Mar. 14, 2019

(65) Prior Publication Data
US 2019/0209224 A1    Jul. 11, 2019

Related U.S. Application Data

(62) Division of application No. 15/138,670, filed on Apr. 26, 2016, now Pat. No. 10,265,111.

(51) Int. Cl.
*A61B 17/88*    (2006.01)

(52) U.S. Cl.
CPC ........ *A61B 17/8855* (2013.01); *A61B 17/885* (2013.01)

(58) Field of Classification Search
CPC ............... A61F 2/441; A61F 2/4455; A61F 2002/4475; A61F 2002/4602; A61F 2002/4631; A61B 17/885; A61B 17/8852; A61B 17/8855; A61B 17/8802; A61B 17/8805; A61B 17/8816; A61B 17/1671; A61B 17/8858
See application file for complete search history.

(56) References Cited

U.S. PATENT DOCUMENTS

| | | |
|---|---|---|
| 3,211,150 A | 10/1965 | Foderick |
| 4,773,393 A | 9/1988 | Haber et al. |
| 5,057,106 A | 10/1991 | Kasevich et al. |
| 5,540,679 A | 6/1996 | Fram et al. |
| 5,843,116 A | 12/1998 | Crocker et al. |
| 6,129,737 A | 10/2000 | Hamilton et al. |
| 6,230,060 B1 | 5/2001 | Mawhinney |
| 6,241,727 B1 | 6/2001 | Tu |
| 6,352,551 B1 | 3/2002 | Wang |
| 6,364,900 B1 | 4/2002 | Heuser |

(Continued)

FOREIGN PATENT DOCUMENTS

| | | |
|---|---|---|
| DE | 10010467 | 9/2001 |
| EP | 1313411 | 10/2007 |

(Continued)

OTHER PUBLICATIONS

International Search Report dated Aug. 8, 2017 of corresponding International Application No. PCT/US2017/029330.

(Continued)

*Primary Examiner* — Kevin T Truong
*Assistant Examiner* — Tracy L Kamikawa

(57) ABSTRACT

An inflatable bone tamp is provided that includes a shaft with proximal and distal portions and a central longitudinal axis. A balloon is attached to the shaft such that a material can flow through the shaft and into the balloon to inflate the balloon. A flow controller controls the flow of the material through the shaft and into the balloon. Kits, systems and methods are disclosed.

16 Claims, 23 Drawing Sheets

(56) References Cited

U.S. PATENT DOCUMENTS

| | | |
|---|---|---|
| 6,416,457 B1 | 7/2002 | Urick et al. |
| 6,427,089 B1 | 7/2002 | Knowlton |
| 6,458,096 B1 | 10/2002 | Briscoe |
| 6,488,653 B1 | 12/2002 | Lombardo |
| 6,527,739 B1 | 3/2003 | Bigus et al. |
| 6,544,224 B1 | 4/2003 | Steese-Bradley |
| 6,847,848 B2 | 1/2005 | Sterzer et al. |
| 6,911,038 B2 | 6/2005 | Mertens |
| 6,951,569 B2 | 10/2005 | Nohilly et al. |
| 7,197,363 B2 | 3/2007 | Prakash et al. |
| 7,261,720 B2 | 8/2007 | Stevens et al. |
| 7,537,580 B2 * | 5/2009 | Willard ............... A61M 25/10 |
| | | 604/96.01 |
| 7,826,904 B2 | 11/2010 | Appling et al. |
| 8,221,349 B2 | 7/2012 | Auyoung et al. |
| 8,241,335 B2 | 8/2012 | Truckai et al. |
| 8,382,746 B2 * | 2/2013 | Williams ........... A61M 25/1034 |
| | | 606/21 |
| 8,679,106 B2 | 3/2014 | Ormsby |
| 8,708,955 B2 | 4/2014 | Tilson et al. |
| 8,945,107 B2 * | 2/2015 | Buckley ............... A61B 18/02 |
| | | 606/21 |
| 2002/0120229 A1 | 8/2002 | Miles et al. |
| 2003/0130664 A1 | 7/2003 | Boucher et al. |
| 2003/0144298 A1 | 7/2003 | Curwen et al. |
| 2004/0106999 A1 | 6/2004 | Mathews |
| 2004/0133254 A1 | 7/2004 | Sterzer |
| 2004/0186471 A1 | 9/2004 | Trieu |
| 2005/0165389 A1 | 7/2005 | Swain |
| 2005/0245896 A1 | 11/2005 | Kucharczyk et al. |
| 2006/0034886 A1 | 2/2006 | Ward et al. |
| 2007/0149963 A1 | 6/2007 | Matsukuma et al. |
| 2008/0249604 A1 | 10/2008 | Donovan |
| 2009/0088788 A1 | 4/2009 | Mouw |
| 2009/0254064 A1 | 10/2009 | Boatman |
| 2009/0299327 A1 | 12/2009 | Tilson |
| 2009/0299373 A1 | 12/2009 | Sisken |
| 2010/0004650 A1 | 1/2010 | Ormsby |
| 2010/0321192 A1 | 12/2010 | Brannan |
| 2011/0028981 A1 | 2/2011 | McKay |
| 2011/0106184 A1 | 5/2011 | Sapida et al. |
| 2011/0125148 A1 | 5/2011 | Turner |
| 2011/0202064 A1 | 8/2011 | O'Halloran et al. |
| 2011/0319880 A1 | 12/2011 | Prakash |
| 2012/0165941 A1 | 6/2012 | Rabiner |
| 2012/0197319 A1 | 8/2012 | Auyoung et al. |
| 2012/0197321 A1 | 8/2012 | Donovan |
| 2012/0203220 A1 | 8/2012 | Brannan et al. |
| 2012/0259326 A1 | 10/2012 | Brannan |
| 2012/0296273 A1 | 11/2012 | Arana et al. |
| 2013/0144298 A1 | 6/2013 | Choi |
| 2013/0237950 A1 | 9/2013 | Gianotti |
| 2013/0238038 A1 | 9/2013 | Auyoung |
| 2013/0256302 A1 | 10/2013 | Chu |
| 2013/0261729 A1 | 10/2013 | Gillick et al. |
| 2014/0128877 A1 | 5/2014 | O'Halloran |
| 2014/0276572 A1 | 9/2014 | Auyoung et al. |
| 2014/0303730 A1 | 10/2014 | McGuire et al. |
| 2014/0316411 A1 | 10/2014 | Day |
| 2014/0371672 A1 * | 12/2014 | Pinchuk ............... A61M 25/04 |
| | | 604/99.02 |
| 2015/0342660 A1 | 12/2015 | Nash |
| 2015/0359432 A1 | 12/2015 | Ehrenreich |

FOREIGN PATENT DOCUMENTS

| | | |
|---|---|---|
| EP | 2853210 | 4/2015 |
| WO | 217801 A2 | 3/2002 |
| WO | 217801 A3 | 3/2002 |
| WO | 2006053312 | 5/2006 |
| WO | 2008026888 | 3/2008 |
| WO | 2013074933 | 5/2013 |

OTHER PUBLICATIONS

Supplementary European Search Report dated Jul. 11, 2018 of corresponding European Application No. 16735443.0.
Extended European Search Report dated Nov. 27, 2019 of corresponding European Application No. 17790239.2.
European Search Search and Opinion for EP17177266 the counterpart application dated Nov. 16, 2017, 9 pages.
Examination Report dated Jan. 28, 2021 of corresponding European Application No. 17790239.2.

* cited by examiner

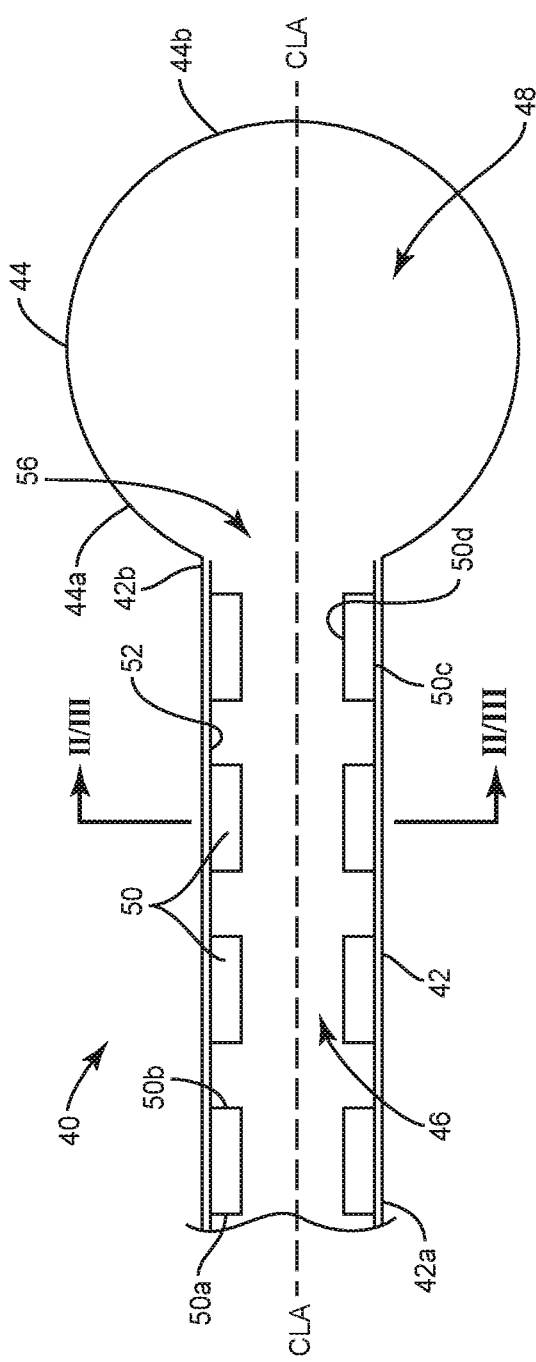
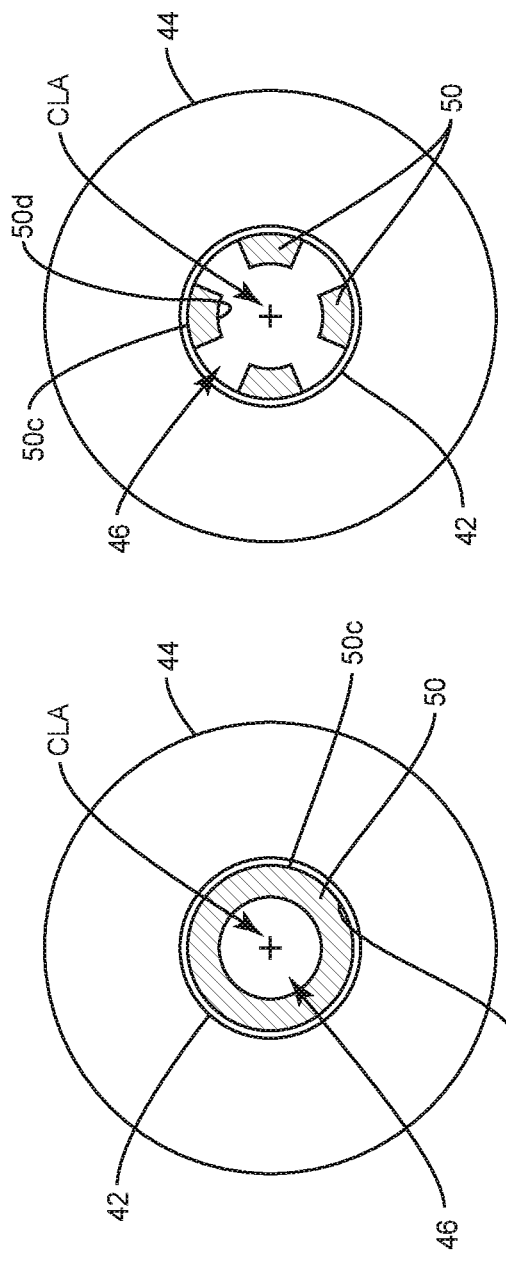

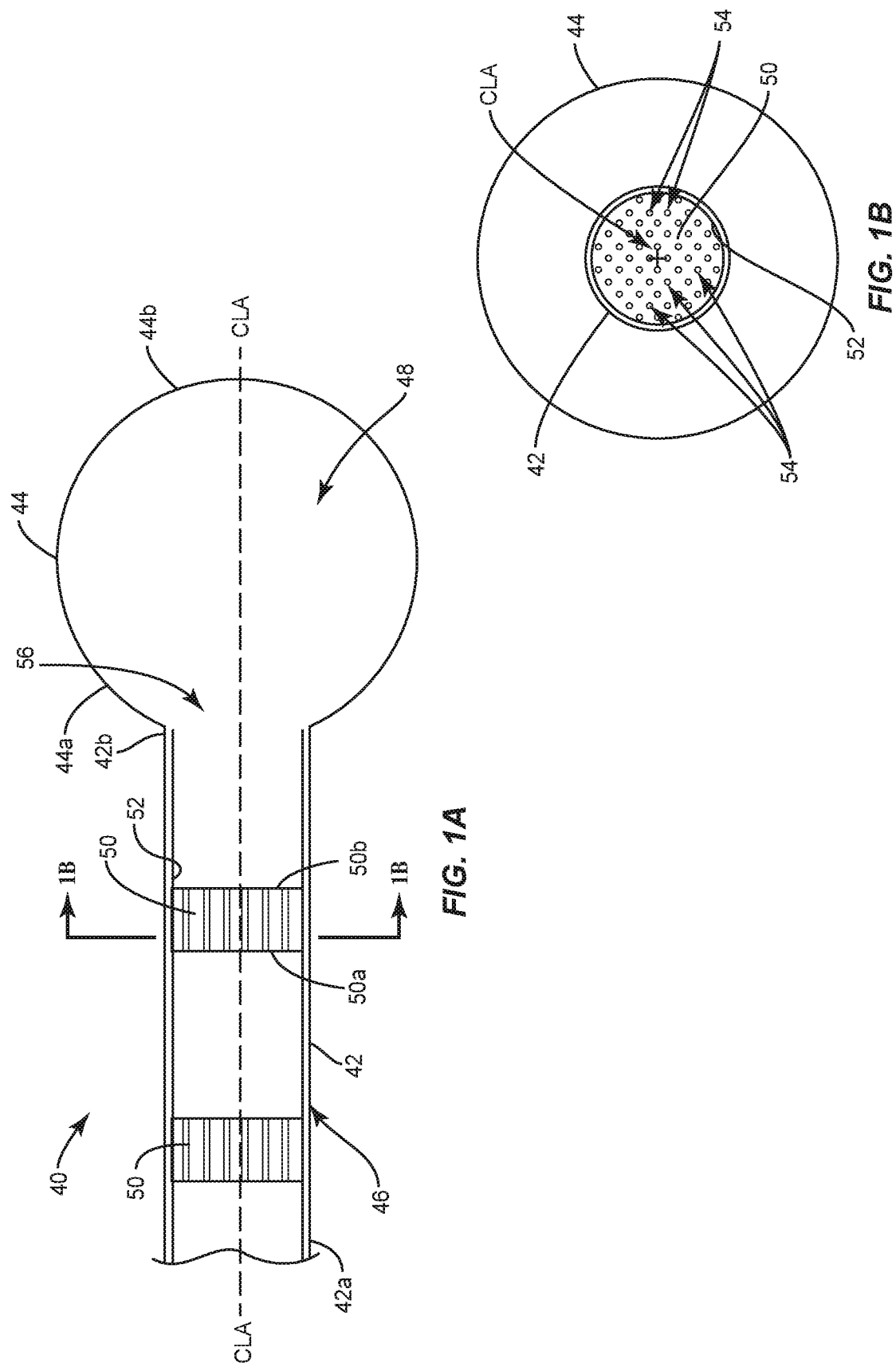

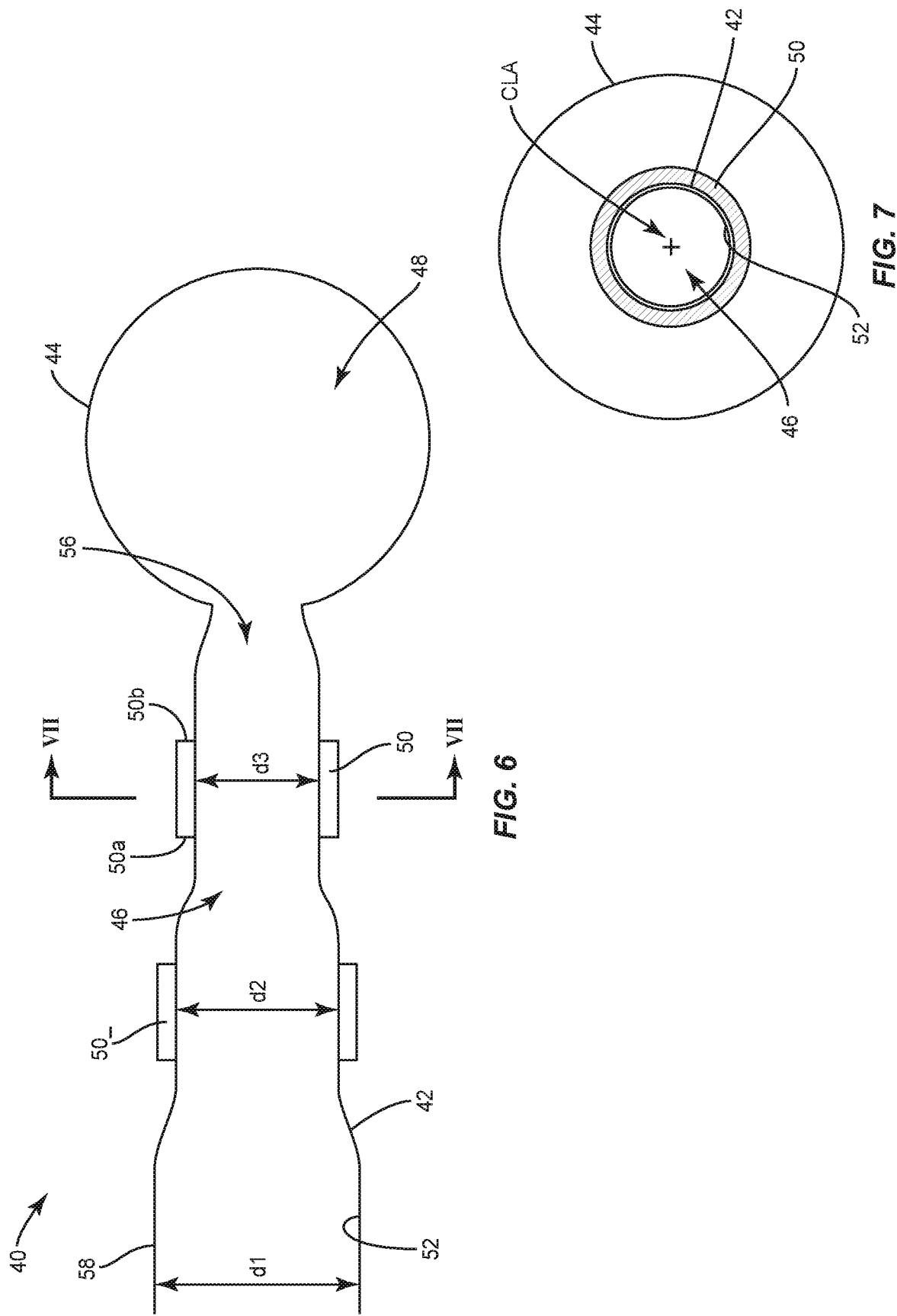

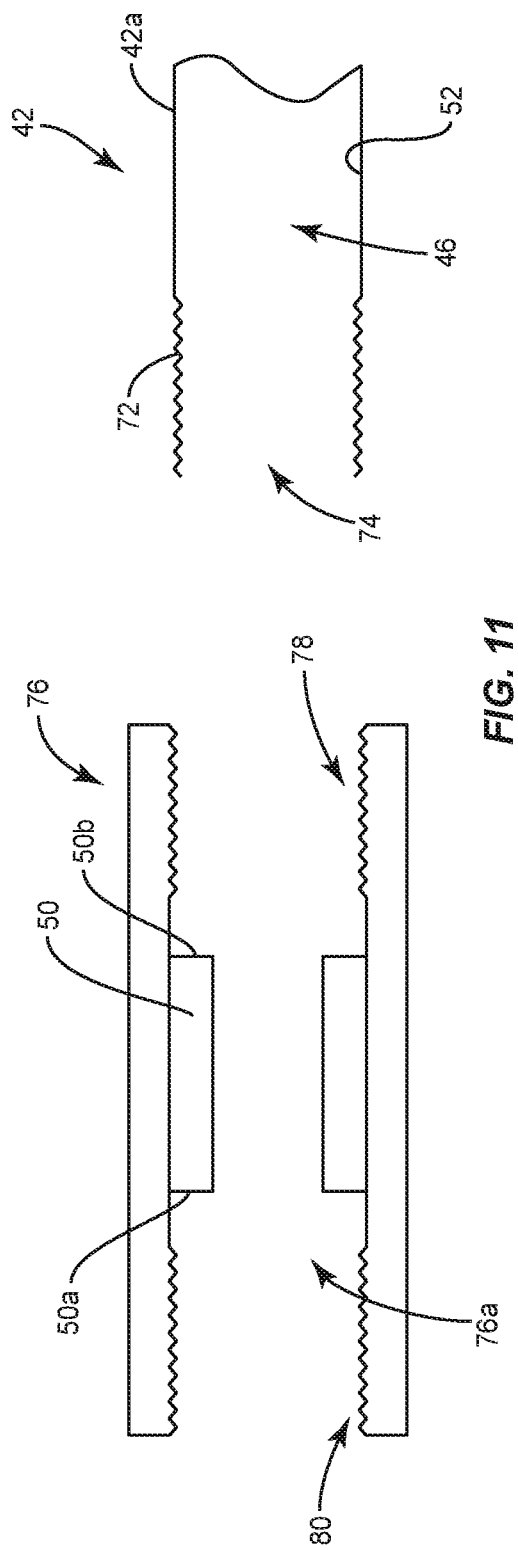
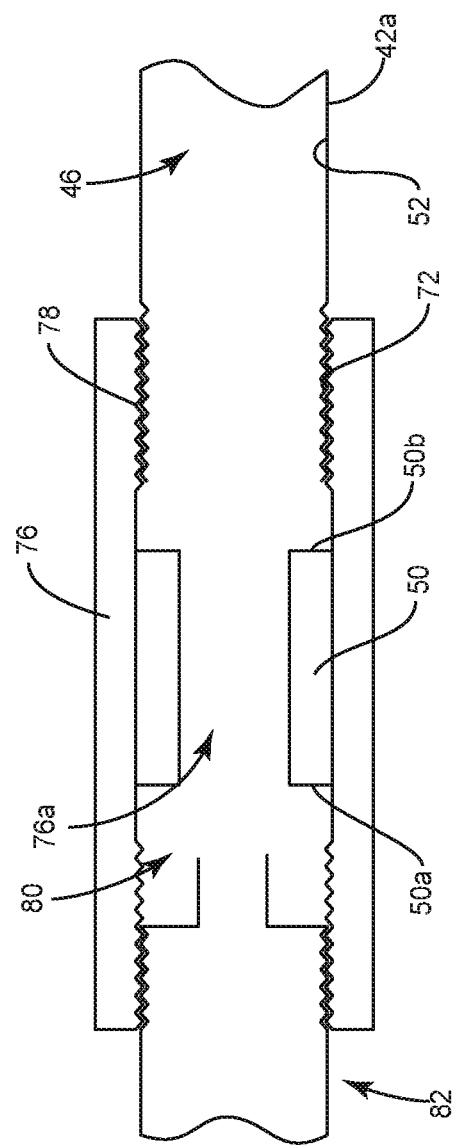
FIG. 11
FIG. 12

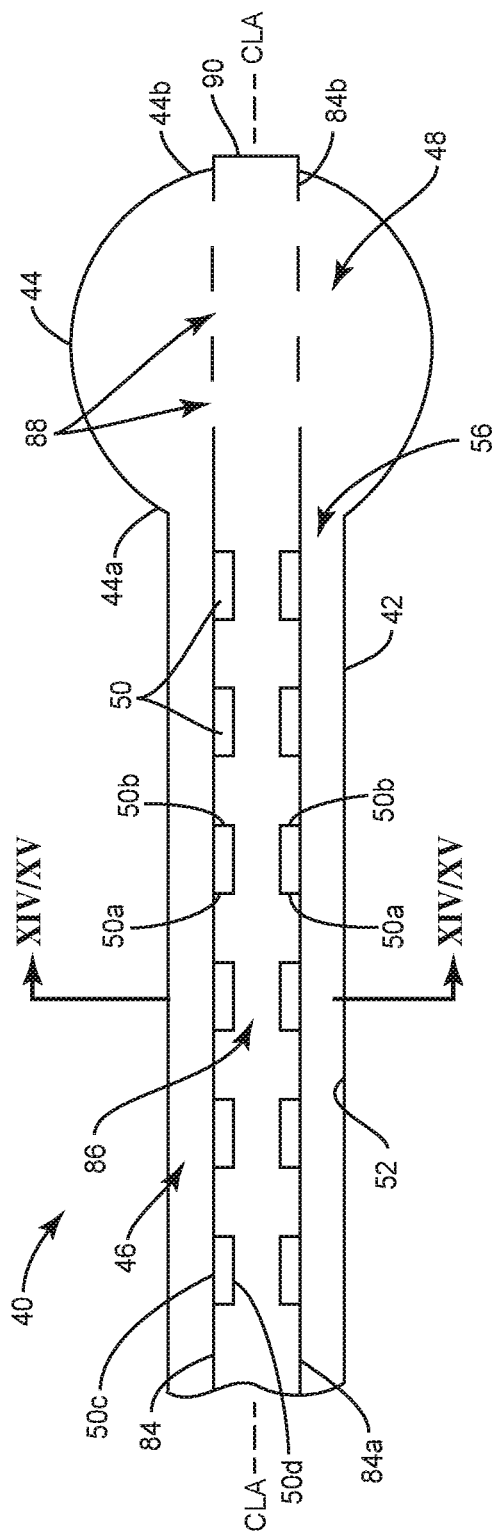
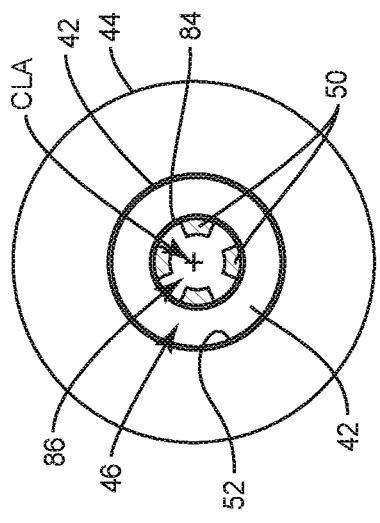
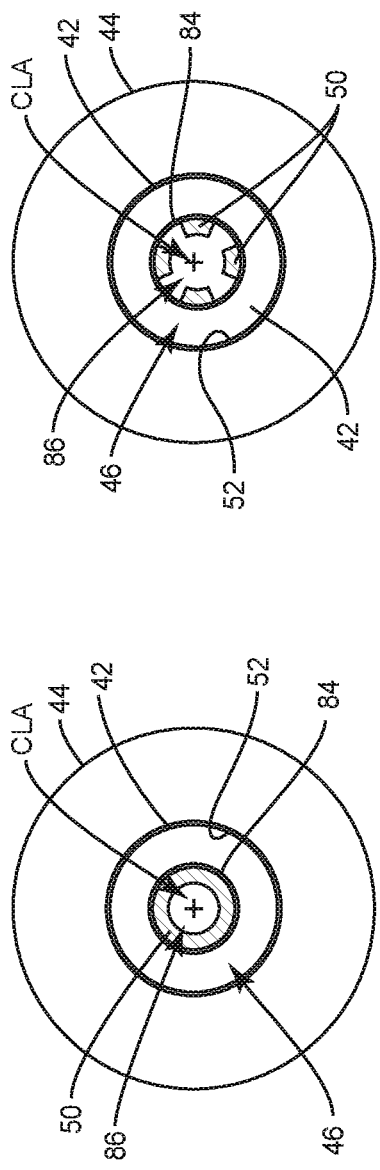
FIG. 13
FIG. 14
FIG. 15

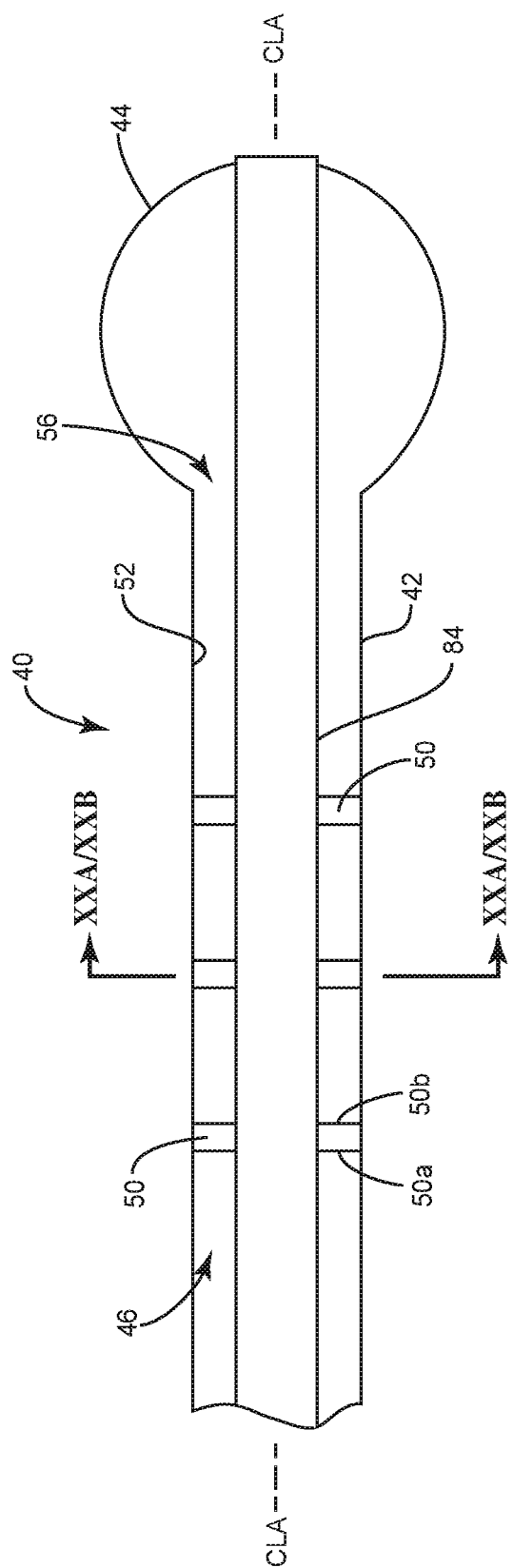
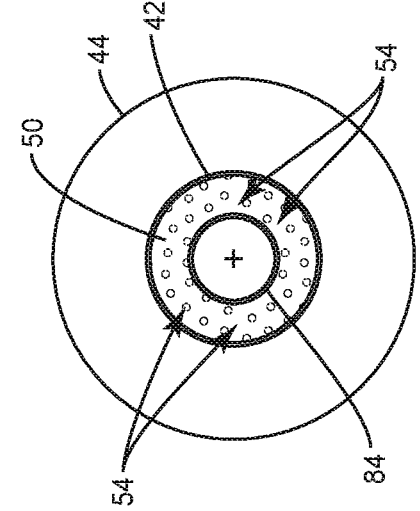
FIG. 19
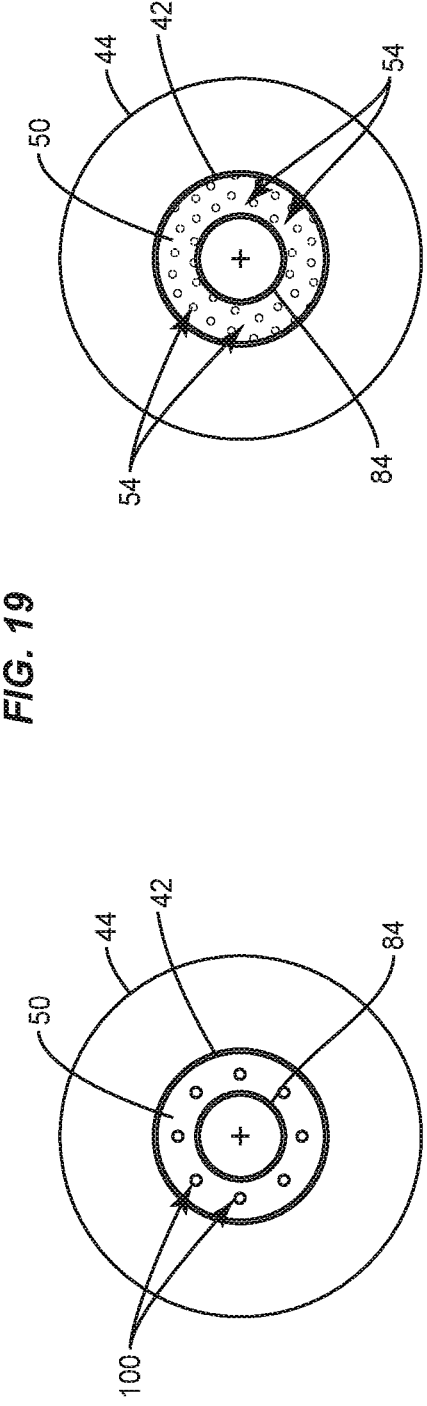
FIG. 20A
FIG. 20B

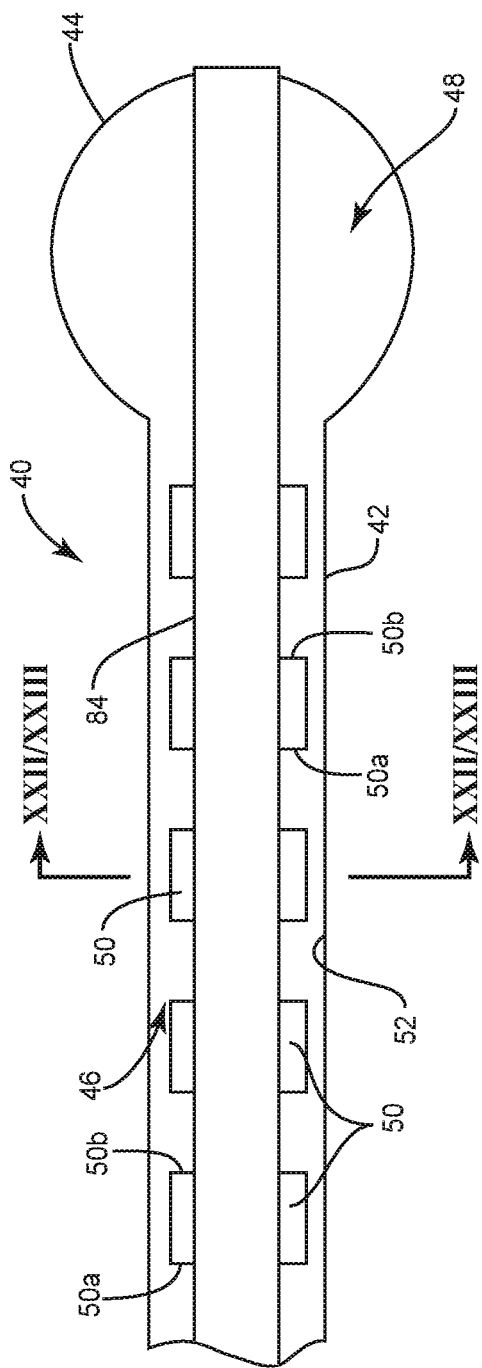
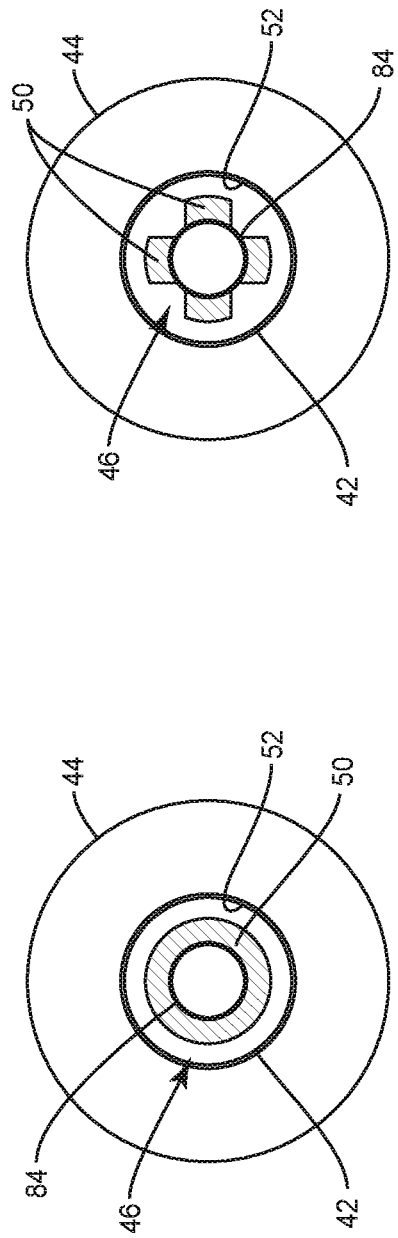
FIG. 21
FIG. 22
FIG. 23

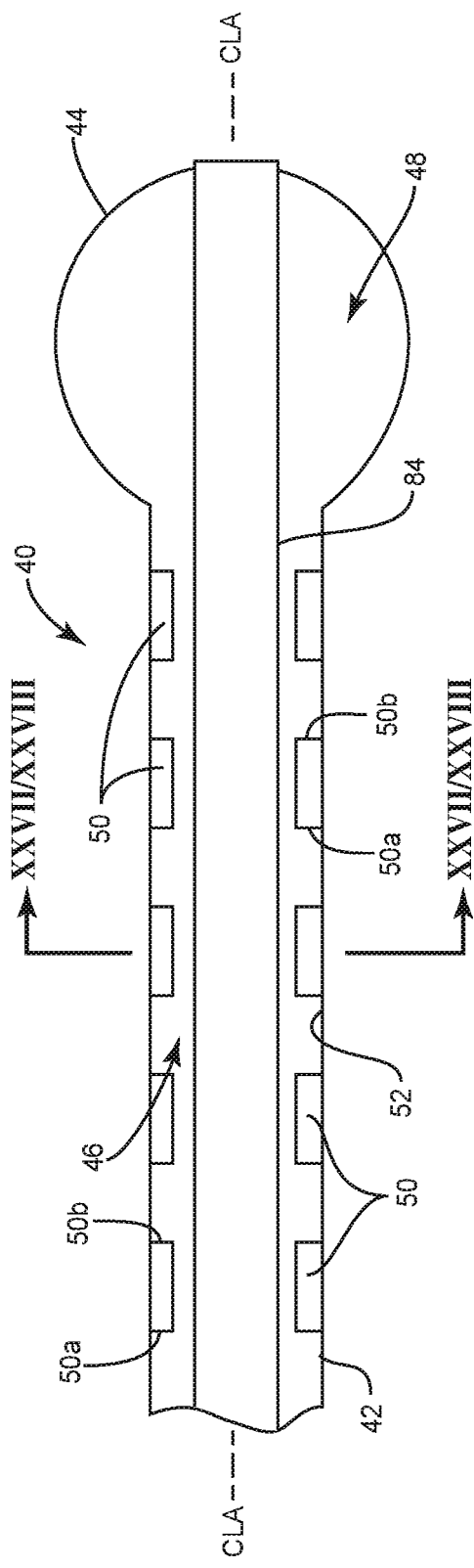
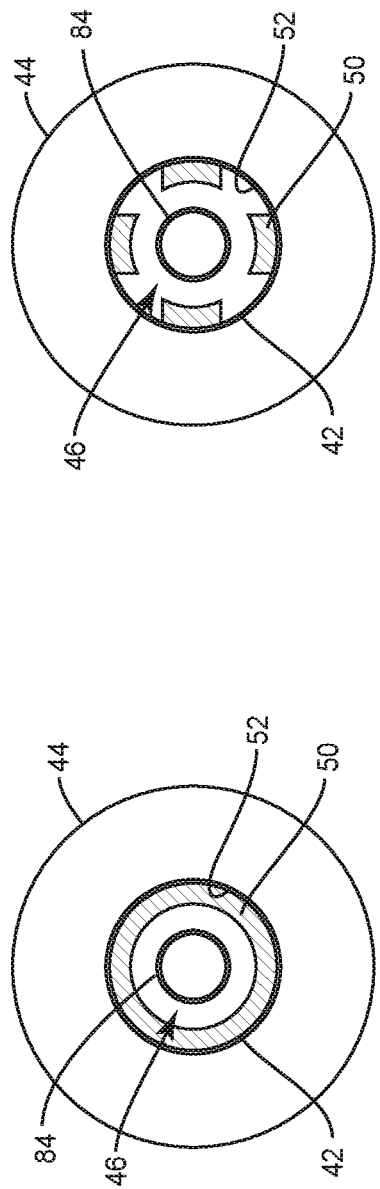
FIG. 26
FIG. 27
FIG. 28

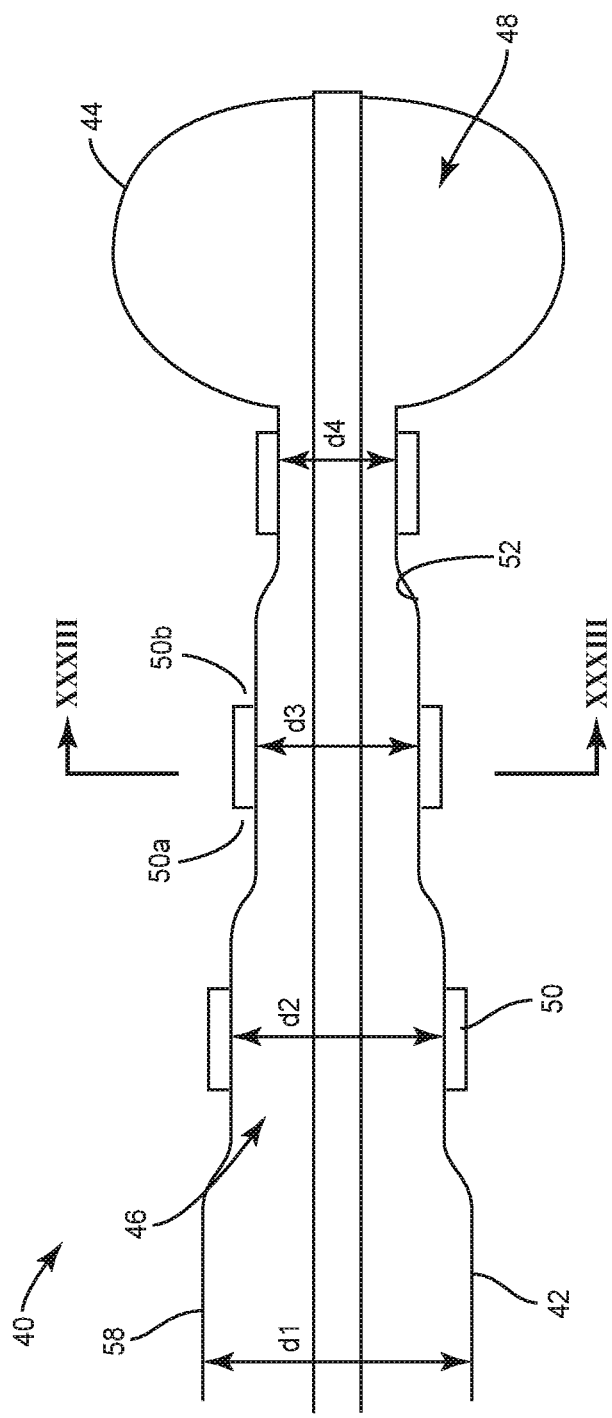
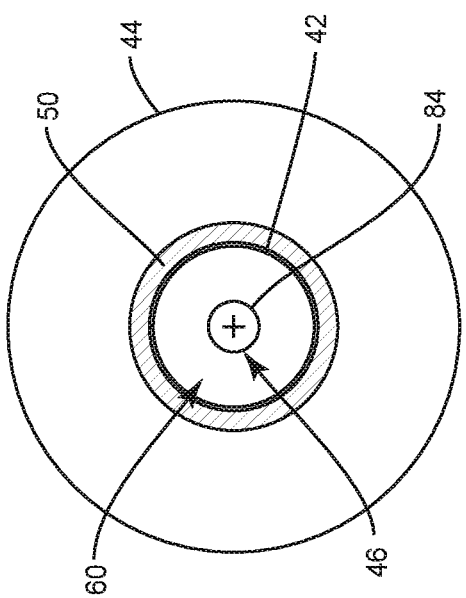

INFLATABLE BONE TAMP WITH FLOW CONTROL AND METHODS OF USE

CROSS-REFERENCE TO RELATED APPLICATIONS

This application is a divisional of U.S. application Ser. No. 15/138,670, filed Apr. 26, 2016, all of which is incorporated by reference herein.

TECHNICAL FIELD

The present disclosure generally relates to medical devices for the treatment of bone disorders, and more particularly to devices and methods for treating spinal disorders, such as, for example, vertebral compression fractures.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

However, conventional spinal fracture treatment procedures lack a means to control the inflation rate of the balloon or balloons. This may lead to uneven inflation, balloon ruptures, or suboptimal balloon performance. To achieve optimal results, there is a need to provide a balloon or balloons that are inflated slowly to allow the balloon or balloons to gradually compress bone and restore height to the vertebral body. Bone is a viscoplastic material that needs time to deform. Fast inflation does not allow the balloon to create a large cavity. Conventional spinal fracture treatment procedures rely on the physician to control the inflation rate of the balloon or balloons. This disclosure describes an improvement over these prior art technologies. Inflating at a lower rate is not typically desired because it leads to a longer procedure time. However, providing a more steady and uniform inflation rate as described herein will lead to better and more predictable patient outcomes.

SUMMARY

New devices and methods are provided for the treatment of bone disorders, and more particularly devices and methods for treating spinal disorders, such as, for example, vertebral compression fractures. In some embodiments, the devices comprise an inflatable bone tamp (IBT) comprising a shaft. A balloon is coupled to the shaft such that a material can flow through the shaft and into the balloon to inflate the balloon. The IBT comprises a flow control device that controls the flow of the material through the shaft and into the balloon.

In some embodiments, the flow control device comprises a flow controller. In some embodiments, the flow control device comprises a plurality of flow controllers. In some embodiments, the IBT comprises a connector that is coupled to the shaft. In some embodiments, the connector is a V-connector. In some embodiments, the flow controller is coupled to the connector. In some embodiments, the flow controller is mounted in the connector.

In some embodiments, the IBT comprises a shaft having a proximal portion, a distal portion, and a central longitudinal axis. In some embodiments, there is an outer shaft and an inner shaft positioned within the outer shaft. The balloon can be coupled to the distal portion of the shaft such that a material can flow through the shaft and into the balloon to inflate the balloon. In some embodiments the balloon can be coupled to the inner shaft and/or the outer shaft. In some embodiments, the flow controller is positioned between the outer shaft and the inner shaft. The flow controller can be coupled to the shaft between the proximal portion and the distal portion that controls the flow of the material through the shaft and into the balloon. In some embodiments, the flow controllers are mounted in the space between the inner shaft and the outer shaft. In some embodiments, the flow controller is coupled to the outer shaft. In some embodiments, the flow controller is mounted in the outer shaft. In some embodiments, the flow controller is coupled to the inner shaft. In some embodiments, the flow controller is mounted in the inner shaft. In some embodiments, the flow controller is crimped onto the inner shaft. In some embodiments, the flow controller is crimped onto the outer shaft. In some embodiments, the flow controller is crimped onto the outer shaft and comprises a plurality of flow controllers that act as flow chokes. There are embodiments where the flow controller comprises a spongiform structure.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 1 is a breakaway, side, cross sectional view of a surgical instrument in accordance with the principles of the present disclosure;

FIG. 1A is a breakaway, side, cross sectional view of one embodiment of the surgical instrument shown in FIG. 1;

FIG. 1B is a cross sectional view of one embodiment of the surgical instrument shown in FIG. 1A;

FIG. 2 is a cross sectional view of one embodiment of the surgical instrument shown in FIG. 1;

FIG. 3 is a cross sectional view of one embodiment of the surgical instrument shown in FIG. 1;

FIG. 6 is a breakaway, side, cross sectional view of a surgical instrument in accordance with the principles of the present disclosure;

FIG. 7 is a cross sectional view of one embodiment of the surgical instrument shown in FIG. 6:

FIG. 11 is a breakaway, side, cross sectional view of components of one embodiment of the surgical instruments shown in FIGS. 1, 6 and 8;

FIG. 12 is breakaway, a side, cross sectional view of the components shown in FIG. 11;

FIG. 13 is a breakaway, side, cross sectional view of a surgical instrument in accordance with the principles of the present disclosure;

FIG. 14 is a cross sectional view of one embodiment of the surgical instrument shown in FIG. 13;

FIG. 15 is a cross sectional view of one embodiment of the surgical instrument shown in FIG. 13;

FIG. 19 is a breakaway, side, cross sectional view of a surgical instrument in accordance with the principles of the present disclosure;

FIG. 20A is a cross sectional view of one embodiment of the surgical instrument shown in FIG. 19;

FIG. 20B is a cross sectional view of one embodiment of the surgical instrument shown in FIG. 19;

FIG. 21 is a breakaway, side, cross sectional view of a surgical instrument in accordance with the principles of the present disclosure;

FIG. 22 is a cross sectional view of one embodiment of the surgical instrument shown in FIG. 21;

FIG. 23 is a cross sectional view of one embodiment of the surgical instrument shown in FIG. 21;

FIG. 26 is a breakaway, side, cross sectional view of a surgical instrument in accordance with the principles of the present disclosure;

FIG. 27 is a cross sectional view of one embodiment of the surgical instrument shown in FIG. 26;

FIG. 28 is a cross sectional view of one embodiment of the surgical instrument shown in FIG. 26;

FIG. 31 is a breakaway, side, cross sectional view of a surgical instrument in accordance with the principles of the present disclosure;

FIG. 32 is a cross sectional view of one embodiment of the surgical instrument shown in FIG. 31;

DETAILED DESCRIPTION

Figure 4:
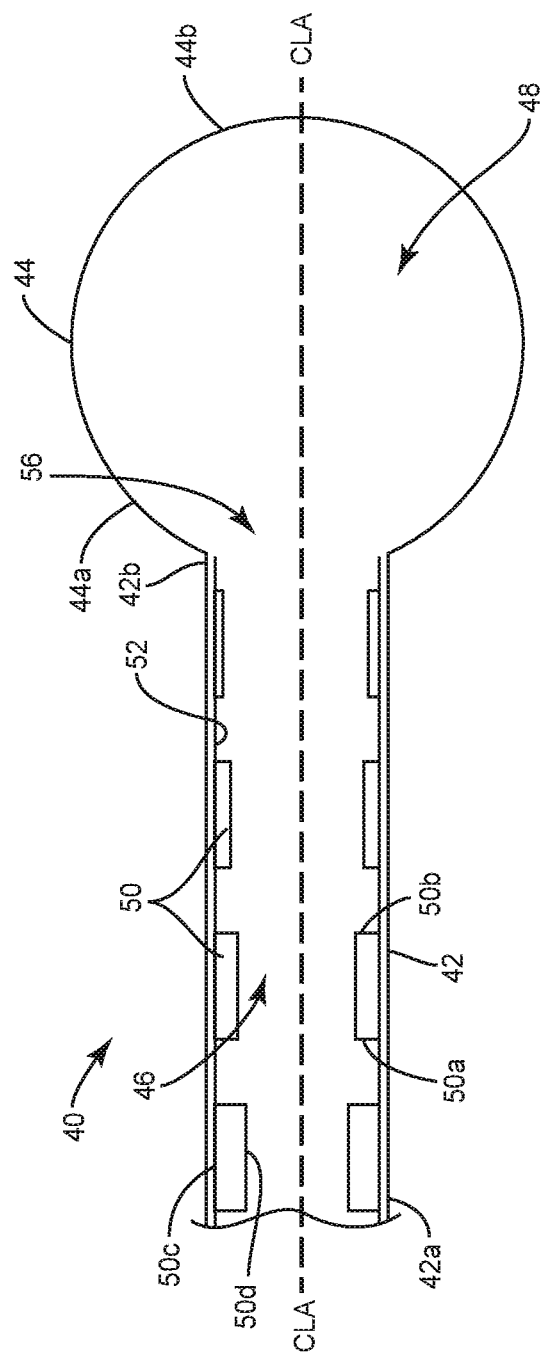
FIG. 4 is a breakaway, side, cross sectional view of one embodiment of the surgical instrument shown in FIG. 1.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" comprises any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be comprised within the invention as defined by the appended claims.

This disclosure is directed to an inflatable bone tamp, such as, for example, a balloon catheter 40. In some embodiments, the components of balloon catheter 40 can be fabricated from biologically acceptable materials suitable for medical applications, including metals, synthetic polymers, ceramics and bone material and/or their composites, depending on the particular application and/or preference of a medical practitioner. For example, the components of balloon catheter 40, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of balloon catheter 40 may have material composites, including the above materials, to achieve various desired characteristics such as strength, rigidity, elasticity, compliance, biomechanical performance, durability and radiolucency or imaging preference. The components of balloon catheter 40, individually or collectively, may also be fabricated from a heterogeneous material such as a combination of two or more of the above-described materials. The components of balloon catheter 40 may be monolithically formed, integrally connected or comprise fastening elements and/or instruments, as described herein.

Balloon catheter 40 comprises an outer shaft or cylindrical portion 42 and a balloon 44 coupled to cylindrical portion 42. In the embodiments shown in FIGS. 1-5, a proximal portion 44a of balloon 44 is coupled to cylindrical portion 42 and an opposite distal portion 44b of balloon 44 is spaced apart from or nonadjacent to the cylindrical portion 42. Cylindrical portion 42 is hollow and defines a passageway 46. In some embodiments, passageway 46 is in communication with an internal chamber 48 of balloon 44. In some embodiments, passageway 46 is configured to for passage of a material to move balloon 44 from an unexpanded configuration, such as, for example, an uninflated configuration to an expanded configuration, such as, for example, an inflated configuration. That is, a material may be moved through passageway 46 and into chamber 48 to move balloon 44 from the uninflated configuration to the inflated configuration. VVhen balloon 44 is in the inflated configuration, balloon 44 has a maximum diameter that is greater than the maximum diameter of balloon 44 when balloon 44 is in the uninflated configuration. In some embodiments, the material is a liquid, such as, for example, a contrast solution, saline or water. In some embodiments, passageway 46 is configured for passage of a material to move balloon 44 from the inflated configuration to the uninflated configuration, as discussed herein. That is, the material moves through passageway 46 to allow balloon 44 to deflate.

In some embodiments, cylindrical portion 42 is a hollow shaft or tube. In some embodiments, cylindrical portion 42 is flexible to allow cylindrical portion 42 to bend as cylindrical portion 42 is navigated through a patient's anatomy. For example, cylindrical portion 42 may be flexible to allow cylindrical portion 42 to be navigated along a curved path created by a medical practitioner in order to position balloon 44 at, in or near a target location or treatment zone, such as, for example, within a vertebral body. In embodiments wherein cylindrical portion 42 is flexible, cylindrical portion 42 can be bent without breaking cylindrical portion 42. In some embodiments, cylindrical portion 42 is rigid such that cylindrical portion 42 cannot be bent without cylindrical portion 42 breaking. For example, cylindrical portion 42 may be rigid to provide strength to cylindrical portion 42 in applications wherein balloon catheter 40 is navigated along a straight path created by a medical practitioner in order to position balloon 44 at, in or near a target location or treatment zone, such as, for example, a space within a vertebral body.

In some embodiments, balloon 44 is made from a resilient biocompatible material. In one embodiment, balloon 44 is a compliant balloon that resists stretching. In one embodiment, balloon 44 comprises polyolefin copolymer (POC), Polyurethane, Nylon. In one embodiment, balloon 44 is a non-compliant or semi-compliant balloon that stretches, at least to some degree. In one embodiment, balloon 44 comprises polyethylene terapthelate (PET). In some embodiments, balloon 44 can have various cross section configurations when balloon 44 is in the inflated configuration, such as, for example, oval, oblong, triangular, rectangular, square, polygonal, irregular, uniform, non-uniform, variable, tubular and/or tapered. In some embodiments, an outer surface of balloon 44 may have various surface configurations, such as, for example, smooth and/or surface configurations to enhance fixation with tissue, such as, for example, rough, arcuate, undulating, porous, semi-porous, dimpled, polished and/or textured.

Balloon 44 can be a single or a multi-layered balloon, where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation.

Balloon catheter 40 comprises one or a plurality of flow controllers 50. In the embodiments shown in FIGS. 1-5, flow controllers 50 are positioned within cylindrical portion 42. In these embodiments, flow controllers 50 are configured to control the flow of the material through passageway 46 as the material travels through passageway 46. In some embodiments, flow controllers 50 directly engage an inner surface 52 of cylindrical portion 42 such that a central portion of passageway 46 is unobstructed along a central longitudinal axis CLA defined by cylindrical portion 42, as shown in FIGS. 1, 2 and 3. In some embodiments, flow controllers 50 directly engage inner surface 52 of cylindrical portion 42 such that at least one of flow controllers 50 block and/or obstruct the central portion of passageway 46 along central longitudinal axis CLA, as shown in FIGS. 1A and 1B.

In some embodiments, flow controllers 50 comprise a material, such as, for example, one of the materials discussed herein. In some embodiments, flow controllers 50 comprise a non-porous material. Flow controller 50 may be comprised a discrete bands concentric to central longitudinal axis CLA or discrete strips that extend parallel to central longitudinal axis CLA, as shown in FIGS. 1-3. In some embodiments, flow controllers 50 comprise a porous material that may be a lattice-like or spongiform structure. In some embodiments, flow controllers 50 comprise a foam material, such as, for example, an open cell foam material or spongiform material/structure. In some embodiments, the open cell foam material or spongiform material/structure comprises one or a plurality of pores 54, as shown in FIG. 1B. In some embodiments, at least one of pores 54 extends through opposite proximal and distal surfaces 50a, 50b a respective flow controller 50. In some embodiments, at least one of pores 54 extends through one of proximal and distal surfaces 50a, 50b without extending through the other one of proximal and distal surfaces 50a, 50b. In some embodiments, at least one of pores 54 is in communication with at least another one of pores 54. In some embodiments, pores 54 are interconnected with one another. In some embodiments, pores 54 are nonadjacent to one another and/or are not in communication with one another.

In some embodiments, balloon catheter 40 comprises one or a plurality of flow controllers 50 that extend continuously from a proximal portion 42a of cylindrical portion 42 to an opposite distal portion 42b of cylindrical portion 42. That is, one or more of flow controllers 50 may have a maximum length along central longitudinal axis CLA that is equal to a maximum length of cylindrical portion 42 along central longitudinal axis CLA. In some embodiments, balloon catheter 40 comprises a single flow controller 50 that that extends continuously from proximal portion 42a to distal portion 42b and also extends 360 degrees about central longitudinal axis CLA, as shown in FIG. 2, for example. In some embodiments, balloon catheter 40 comprises a plurality of flow controllers 50 that extends continuously from proximal portion 42a to distal portion 42b and are nonadjacent to one another or spaced apart about a circumference of cylindrical portion 42, as shown in FIG. 3. Flow Controllers 50 can be comprised of discrete strips coupled along the shaft parallel to the central longitudinal axis. Flow controllers 50 each can have a height defined between opposite first and second surfaces 50c, 50d. The flow controllers can be comprised of discrete bands that are concentric to central longitudinal axis CLA, as shown in FIG. 1. In some embodiments, the flow controller can be discrete strips coupled along the shaft that extend continuously from proximal portion 42a to distal portion 42b with a uniform height from proximal portion 42a to distal portion 42b. In some embodiments, the flow controller 50 can be discrete strips that extend continuously from proximal portion 42a to distal portion 42b taper from proximal portion 42a to distal portion 42b. In some embodiments, the flow controller(s) 50 that extend(s) continuously from proximal portion 42a to distal portion 42b taper from distal portion 42b to proximal portion 42a.

In some embodiments, balloon catheter 40 comprises a plurality of flow controllers 50 that are nonadjacent to one another or spaced apart along central longitudinal axis CLA, as shown in FIG. 1. In some embodiments, flow controllers 50 are discrete bands concentric to central longitudinal axis CLA. In some embodiments, the spaced apart flow controllers 50 are uniformly nonadjacent to one another or spaced apart along central longitudinal axis CLA. In some embodiments, at least one of the spaced apart flow controllers 50 extends 360 degrees about central longitudinal axis CLA, as shown in FIG. 2, for example. In such embodiments, flow controllers 50 are discrete bands concentric to central longitudinal axis CLA. In some embodiments, the spaced apart flow controllers 50 are nonadjacent to one another or spaced apart along central longitudinal axis CLA, as shown in FIG. 1 and are also nonadjacent to one another or spaced apart about a circumference of cylindrical portion 42, as shown in FIG. 3. In such embodiments, flow controllers 50 are discrete strips that extend parallel to central longitudinal axis CLA.

Figure 5:
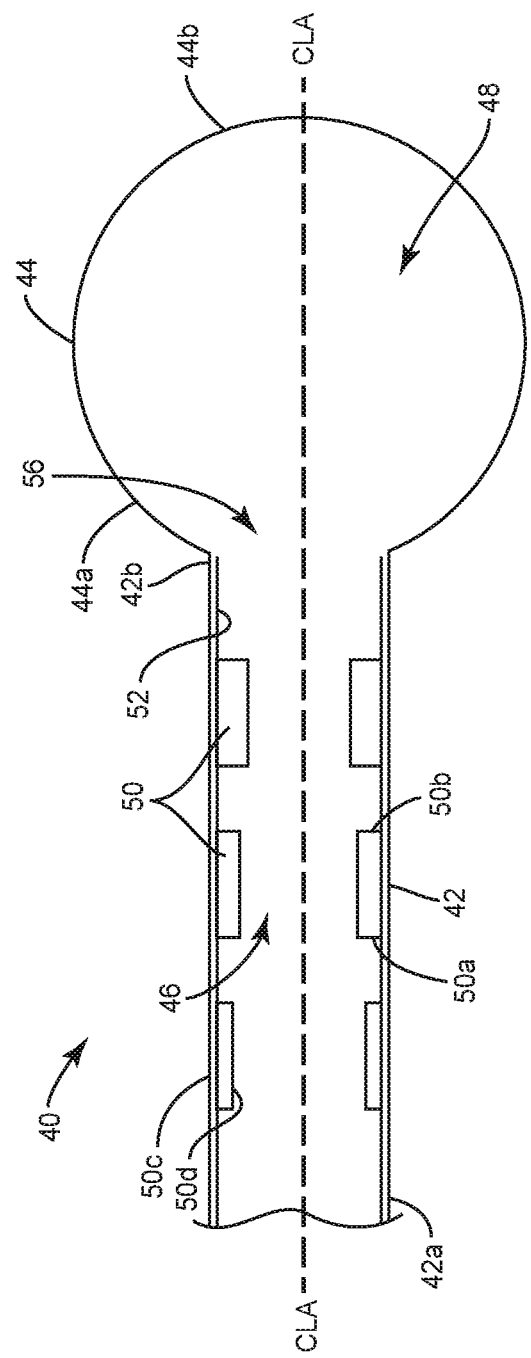
FIG. 5 is a breakaway, side, cross sectional view of one embodiment of the surgical instrument shown in FIG. 1.

In the embodiments shown in FIGS. 1-5, first surfaces 50c of the spaced apart flow controllers 50 engage inner surface 52 of cylindrical portion 42. In some embodiments, the spaced apart or discrete flow controllers 50 are each tapered from proximal portion 50a to distal portion 50b. In some embodiments, the discrete flow controllers 50 are each tapered from distal portion 50b to proximal portion 50a. In some embodiments, each of the discrete flow controllers 50 have the same height, as shown in FIG. 1. In some embodiments, each of the spaced apart flow controllers 50 have a different height, wherein the flow controller 50 having the greatest height is positioned at proximal portion 42a of cylindrical portion 42 and the flow controller having the least height is positioned at distal portion 42b of cylindrical portion 42, as shown in FIG. 4. In some embodiments, each of the spaced apart flow controllers 50 have a different height, wherein the flow controller 50 having the greatest height is positioned at distal portion 42b of cylindrical portion 42 and the flow controller 50 having the least height is positioned at proximal portion 42a of cylindrical portion 42, as shown in FIG. 5. The height(s) of the flow controller(s) 50 between the flow controllers 50 with the greatest and least heights is less than the height of the flow controller 50 with the greatest height and greater than the flow controller 50 with the least height such that flow controllers 50 have a stepped configuration, as shown in FIGS. 4 and 5.

In use, to treat a bone disorder, such as, for example, a spinal fracture, a medical practitioner obtains access to a target location including at least one vertebra, such as, for example, a fractured vertebra, in any appropriate manner, such as through incision and retraction of tissue. It is envisioned that the balloon catheter 40 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Balloon catheter 40 is moved through the incision and positioned so that balloon 44 is positioned within a vertebral body of the fractured vertebra. In some embodiments, balloon 44 is moved into the vertebral body when balloon 44 is in the uninflated configuration. An inflation material, such as, for example, one of the materials discussed above is moved through passageway 46 such that the material flows through passageway 46, out of an opening 56 in distal portion of cylindrical portion 42 and into cavity 48 of balloon 44 to move balloon 44 from the uninflated configuration to the inflated configuration. As the material flows through passageway 46, flow controller(s) 50 reduce(s) the rate of flow of the material to prevent balloon 44 from being inflated too quickly. That is, flow controller(s) ensure(s) that balloon 44 is gradually inflated such that balloon 44 pushes cancellous bone of the vertebral body towards cortical walls of the vertebral body to form a cavity within the vertebral body. In some embodiments, the cavity created by balloon 44 is filled with a material, such as, for example, bone cement. In some embodiments, opening 56 is coaxial with central longitudinal axis CLA.

In one embodiment, shown in FIG. 6, balloon catheter 40 comprises one or a plurality of flow controllers 50 coupled to an outer surface 58 of cylindrical portion 42. In such embodiments, flow controllers 50 may be discrete bands concentric to central longitudinal axis CLA or discrete strips that extend parallel to central longitudinal axis CLA. In some embodiments, flow controllers 50 are crimped to outer surface 58. At each position along cylindrical portion 42 to which flow controllers 50 are crimped, the diameter of cylindrical portion 42 decreases. For example, cylindrical portion 42 comprises a first portion that is free of any flow controllers 50 and has an inner diameter d1 and a second portion that comprises at least one flow controller 50 and has an inner diameter d2 that is less than inner diameter d1. In some embodiments, cylindrical portion 42 comprises a third portion that comprises at least one additional flow controller 50 and has an inner diameter d3 that is less than inner diameter d2. In some embodiments, each of flow controllers 50 extends 360 degrees about central longitudinal axis CLA, as shown in FIG. 7, for example.

The changes in the inner diameter of cylindrical portion 42 between inner diameter d1, inner diameter d2 and inner diameter d3 controls the flow of the inflation material through passageway 46 to gradually inflate balloon 44. In particular, as the inflation material flows through passageway 46, the changes in the inner diameter of cylindrical portion 42 reduce the rate of flow of the material to prevent balloon 40 from being inflated too quickly. That is, the changes in the inner diameter of cylindrical portion 42 ensure that balloon 44 is gradually inflated such that balloon 44 pushes cancellous bone of the vertebral body towards cortical walls of the vertebral body to form a cavity within the vertebral body.

Figure 8:
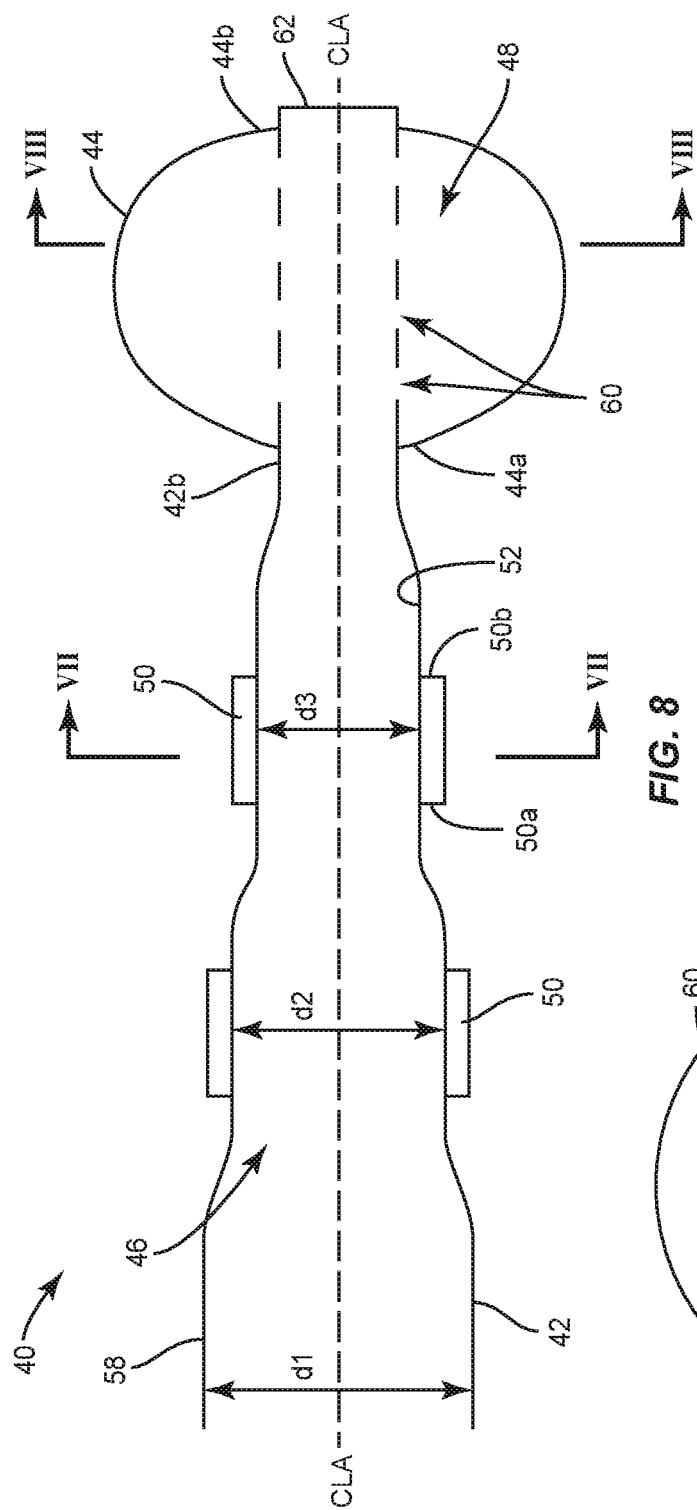
FIG. 8 is a breakaway, side, cross sectional view of a surgical instrument in accordance with the principles of the present disclosure.
Figure 9:
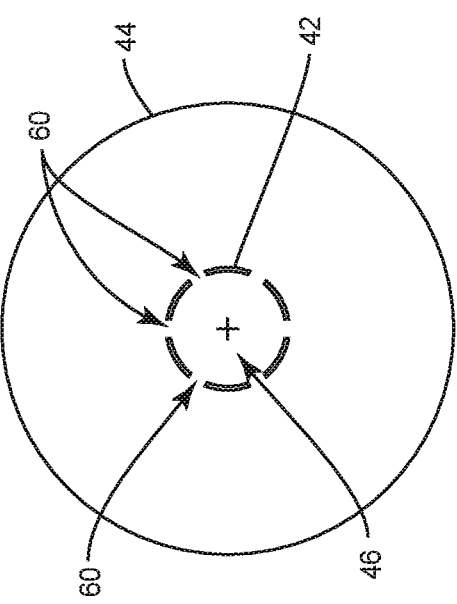
FIG. 9 is a cross sectional view of one embodiment of the surgical instrument shown in FIG. 8.

In one embodiment, shown in FIG. 8, proximal portion 44a of balloon 44 is coupled to a first section of distal portion 42b of cylindrical portion 42 and distal portion 44b of balloon 44 is coupled to a second section of distal portion 42b. Distal portion 42b comprises one or a plurality of apertures 60 that extend through inner and outer surfaces 52, 58 of cylindrical portion 42. Cylindrical portion 42 comprises an end wall 62 that defines a distal limit of passageway 46. Apertures 60 are in communication with passageway 46 and cavity 48 of balloon 44 such that the inflation material can move out of passageway 46 and into cavity 48 through apertures 60 to inflate balloon 44. In some embodiments, apertures 60 are nonadjacent to one another or spaced apart radially about a circumference of cylindrical portion 42, as shown in FIG. 9. In some embodiments, at least one of apertures 60 may have various cross section configurations, such as, for example, circular, oval, oblong, triangular, rectangular, square, polygonal, irregular, uniform, non-unifomi, variable and/or tapered. In some embodiments, at least one of apertures 60 may be disposed at alternate orientations, relative to central longitudinal axis CLA, such as, for example, transverse, perpendicular and/or other angular orientations such as acute or obtuse, co-axial and/or may be offset or staggered.

As shown in FIG. 8, flow controllers 50 are coupled to outer surface 58 of cylindrical portion 42, similar to the embodiment shown in FIG. 6 such that the inner diameter of cylindrical portion 42 changes between inner diameter d1, inner diameter d2 and inner diameter d3 controls the flow of the inflation material through passageway 46 to gradually inflate balloon 44. In particular, as the inflation material flows through passageway 46, the changes in the inner diameter of cylindrical portion 42 reduce the rate of flow of the material so when the material flows through apertures 60 and into cavity 48 of balloon 44, the inflation material does not to inflate balloon 40 too quickly. That is, the changes in the inner diameter of cylindrical portion 42 ensure that balloon 44 is gradually inflated such that balloon 44 pushes cancellous bone of the vertebral body towards cortical walls of the vertebral body to form a cavity within the vertebral body. In such embodiments, flow controllers 50 may be discrete bands concentric to central longitudinal axis CLA.

Figure 10:
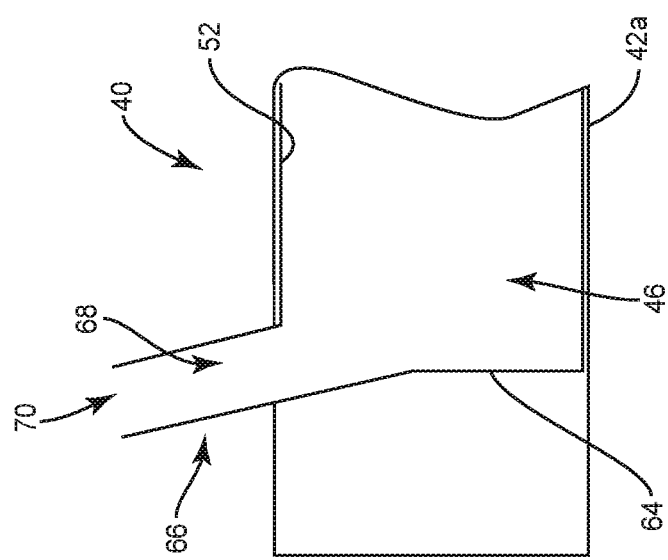
FIG. 10 is a breakaway, side, cross sectional view of a portion of one embodiment of the surgical instruments shown in FIGS. 1, 6 and 8.

In some embodiments, proximal portion 42a of cylindrical portion 42 of at least one of balloon catheters 40 shown in FIGS. 1, 6 and 8 comprises an end wall 64 that defines a proximal limit of passageway 46 and a port 66 having a lumen 68 that is in communication with passageway 46, as shown in FIG. 10. The inflation material may be injected into passageway 46 by positioning an inflation material delivery device, such as, for example, a syringe adjacent to port 66 and ejecting the inflation material from the delivery device such that the inflation material moves through an opening 70 of port 66 and lumen 68 of port 66.

In some embodiments, proximal portion 42a of cylindrical portion 42 of at least one of balloon catheters 40 shown in FIGS. 1, 6 and 8 comprises a threaded portion 72 and an opening 74 that is in communication with passageway 46, as shown in FIG. 11. Balloon catheter 40 further comprises a connector 76 having an inner surface defining a channel 76a having a threaded section 78 and a threaded section 80 that is nonadjacent to or spaced apart from threaded section 78, as shown in FIG. 11. In some embodiments, connector 76 comprises one or a plurality of flow controllers 50 within channel 76a. In some embodiments, flow controllers 50 are positioned between threaded sections 78, 80. Threaded portion 72 of cylindrical portion 42 is configured to engage threaded section 78 of connector 76 to couple cylindrical portion 42 to connector 76, as shown in FIG. 12, Threaded section 80 of connector 76 is configured to engage a threaded section of an inflation material delivery device, such as, for example, a syringe 82, as also shown in FIG. 12. In some embodiment, an inflation material is ejected from syringe 82 and into channel 76a of connector 76. Flow controller(s) 50 within channel 76 limit(s) the rate of flow of the material through channel 76. The material flows from channel 76a and into passageway 46. In some embodiments, connector 76 can be variously connected with cylindrical portion 42 and/or syringe 82, such as, for example, monolithic, integral connection, frictional engagement, threaded engagement, mutual grooves, screws, adhesive, nails, barbs and/or raised element.

In some embodiments, balloon catheter 40 comprises an inner shaft 84 positioned within cylindrical portion 42, as shown in FIGS. 13-18, for example. A distal portion of inner shaft 84 extends through opening 56 of cylindrical portion 42 such that at least a portion of the distal portion of inner shaft 84 is positioned outside of passageway 46 of cylindrical portion 42. Proximal portion 44a of balloon 44 is coupled to distal portion 42b of cylindrical portion 42 and distal portion 44b of balloon 44 is coupled to inner shaft 84. In some embodiments, inner shaft 84 comprises an inner surface defining a lumen 86 and one or a plurality of apertures 88 that are in communication with lumen 86 and cavity 48 of balloon 44 such that an inflation material can be moved through lumen 86 and apertures 88 and into cavity 48 to inflate balloon 44. Inner shaft 84 comprises an end wall 90 that defines a distal limit of lumen 86. In some embodiments, apertures 88 are spaced apart from one another radially about a circumference of inner shaft 84, similar to apertures 60 shown in FIG. 9.

Figure 13A:
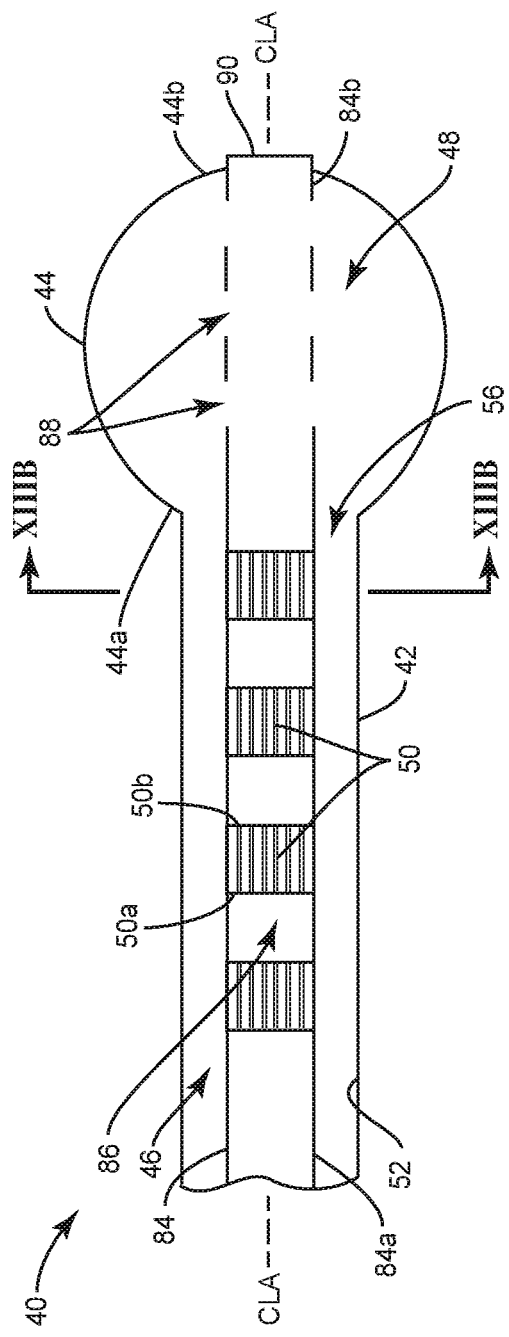
FIG. 13A is a breakaway, side, cross sectional view of one embodiment of the surgical instrument shown in FIG. 1.
Figure 13B:
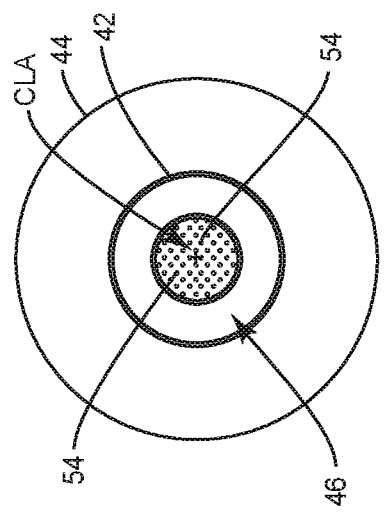
FIG. 13B is a cross sectional view of one embodiment of the surgical instrument shown in FIG. 13A.

One or a plurality of flow controllers 50 are positioned within lumen 86. In the embodiments shown in FIGS. 13-18, flow controllers 50 are configured to control the flow of the material through lumen 86 as the inflation material travels through lumen 86. In some embodiments, flow controllers 50 directly engage an inner surface of inner shaft 84 such that a central portion of lumen is unobstructed along central longitudinal axis CLA, as shown in FIGS. 13, 14 and 15. In some embodiments, flow controllers 50 directly engage the inner surface of inner shaft 84 such that at least one of flow controllers 50 block and/or obstruct the central portion of lumen 86 along central longitudinal axis CLA, as shown in FIGS. 13A and 13B.

In some embodiments, balloon catheter 40 comprises one or a plurality of flow controllers 50 within lumen 86 that extend continuously from a proximal portion 84a of inner shaft 84 to an opposite distal portion 84b of inner shaft 84. That is, one or more of flow controllers 50 within lumen 86 may have a maximum length along central longitudinal axis CLA that is equal to a maximum length of inner shaft 84 along central longitudinal axis CLA. In some embodiments, balloon catheter 40 comprises a single flow controller 50 within lumen 86 that that extends continuously from proximal portion 84a to distal portion 84b and also extends 360 degrees about central longitudinal axis CLA, as shown in FIG. 14, for example. In some embodiments, balloon catheter 40 comprises a plurality of flow controllers 50 within lumen 86 that each extend continuously from proximal portion 84a to distal portion 84b and are spaced apart from one another about a circumference of inner shaft 84, as shown in FIG. 15. In some embodiments, the flow controller(s) 50 within lumen 86 that extend(s) continuously from proximal portion 84a to distal portion 84b has/have a uniform height from proximal portion 84a to distal portion 84b. In some embodiments, the flow controller(s) 50 within lumen 86 that extend(s) continuously from proximal portion 84a to distal portion 84b taper(s) from proximal portion 84a to distal portion 84b. In some embodiments, the flow controller(s) 50 within lumen 86 that extend(s) continuously from proximal portion 84a to distal portion 84b taper(s) from distal portion 84b to proximal portion 84a.

In some embodiments, balloon catheter 40 comprises a plurality of flow controllers 50 within lumen 86 that are spaced apart from one another along central longitudinal axis CLA, as shown in FIG. 13. In such embodiments, flow controllers 50 may be discrete bands concentric to central longitudinal axis CLA or discrete strips that extend parallel to central longitudinal axis CLA. In some embodiments, the spaced apart flow controllers 50 within lumen 86 are uniformly spaced apart from one another along central longitudinal axis CLA. In some embodiments, at least one of the spaced apart flow controllers 50 within lumen 86 extends 360 degrees about central longitudinal axis CLA, as shown in FIG. 14, for example. In such embodiments, flow controllers 50 are discrete bands concentric to central longitudinal axis CLA. In some embodiments, the spaced apart flow controllers 50 within lumen 86 are spaced apart from one another along central longitudinal axis CLA, as shown in FIG. 13 and are also spaced apart from one another about a circumference of inner shaft 84, as shown in FIG. 15. In such embodiments, flow controllers 50 are discrete strips that extend parallel to central longitudinal axis CLA.

In the embodiments shown in FIGS. 13-17, first surfaces 50c of the spaced apart flow controllers 50 within lumen 86 engage the inner surface of inner shaft 84.

Figure 16:
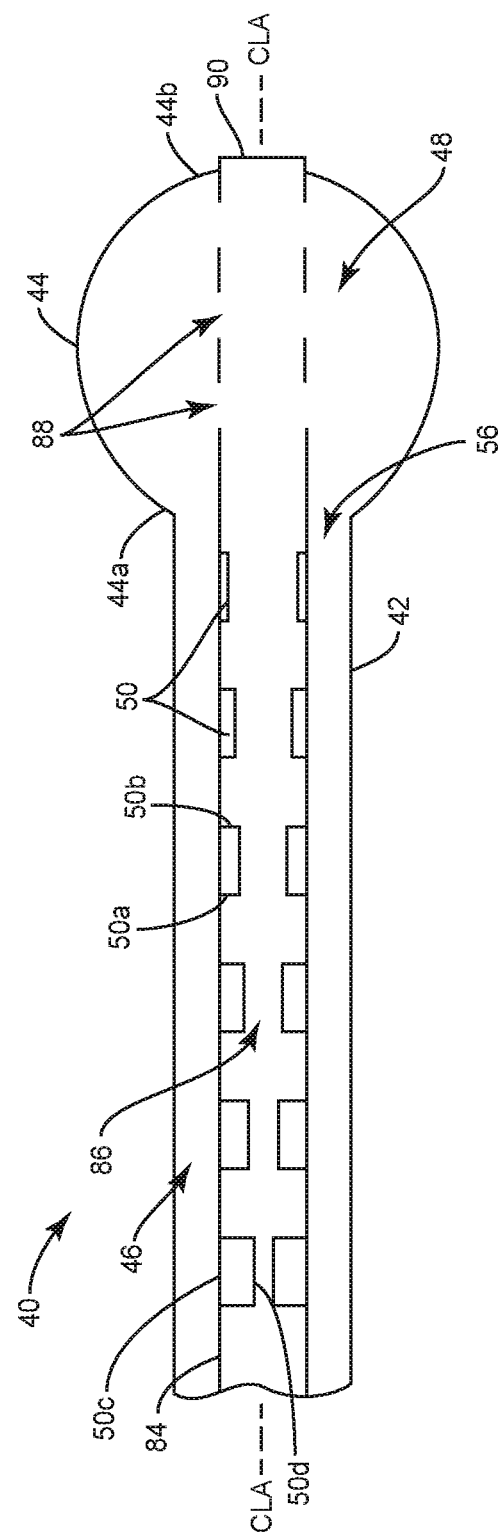
FIG. 16 is a breakaway, side, cross sectional view of one embodiment of the surgical instrument shown in FIG. 15.
Figure 17:
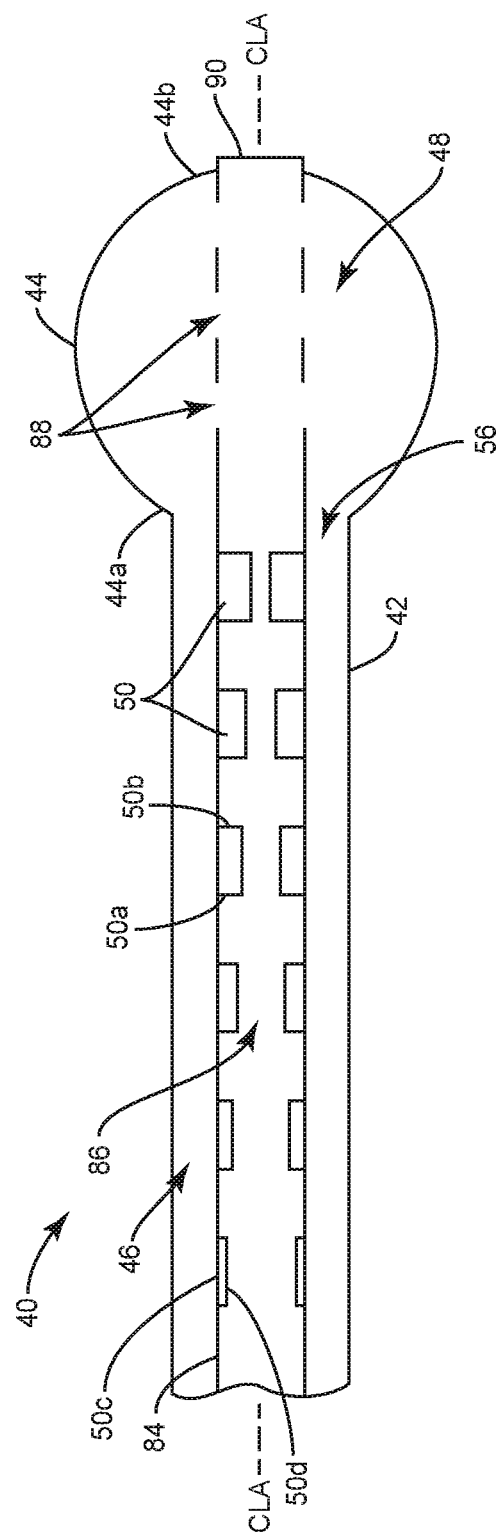
FIG. 17 is a breakaway, side, cross sectional view of one embodiment of the surgical instrument shown in FIG. 15.

In some embodiments, the spaced apart flow controllers 50 within lumen 86 are each tapered from proximal portion 50a to distal portion 50b. In some embodiments, the spaced apart flow controllers 50 within lumen 86 are each tapered from distal portion 50b to proximal portion 50a. In some embodiments, each of the spaced apart flow controllers 50 within lumen 86 has the same height, as shown in FIG. 13. In some embodiments, each of the spaced apart flow controllers 50 within lumen 86 has a different height, wherein the flow controller 50 having the greatest height is positioned at proximal portion 84a of inner shaft 84 and the flow controller 50 having the least height is positioned at distal portion 84b of inner shaft, as shown in FIG. 16. In some embodiments, each of the spaced apart flow controllers 50 within lumen 86 has a different height, wherein the flow controller 50 having the greatest height is positioned at distal portion 84b of inner shaft 84 and the flow controller 50 having the least height is positioned at proximal portion 84a of inner shaft 84, as shown in FIG. 17. The height(s) of the flow controller(s) 50 within lumen 86 between the flow controllers 50 with the greatest and least heights is less than the height of the flow controller 50 with the greatest height and greater than the flow controller 50 with the least height such that flow controllers 50 have a stepped configuration, as shown in FIGS. 16 and 17.

In use, to treat a bone disorder, such as, for example, a spinal fracture, a medical practitioner obtains access to a target location including at least one vertebra, such as, for example, a fractured vertebra, in any appropriate manner, such as through incision and retraction of tissue. Balloon catheter 40 is moved through the incision and positioned so that balloon 44 is positioned within a vertebral body of the fractured vertebra. In some embodiments, balloon 44 is moved into the vertebral body when balloon 44 is in the uninflated configuration. An inflation material, such as, for example, one of the materials discussed above is moved through lumen 86 such that the material flows through lumen 86, out of apertures 88 and into cavity 48 of balloon 44 to move balloon 44 from the uninflated configuration to the inflated configuration. As the material flows through lumen 86, flow controller(s) 50 reduce(s) the rate of flow of the material to prevent balloon 44 from being inflated too quickly. That is, flow controller(s) 50 ensure(s) that balloon 44 is gradually inflated such that balloon 44 pushes cancellous bone of the vertebral body towards cortical walls of the vertebral body to form a cavity within the vertebral body. In some embodiments, the cavity created by balloon 44 is filled with a material, such as, for example, bone cement. In some embodiments, the inflation material fills passageway 46 before or after the inflation material moves balloon 44 from the uninflated configuration to the inflated configuration, as discussed herein. In some embodiments, the inflation material moves out of passageway 46 after the inflation material moves balloon 44 from the uninflated configuration to the inflated configuration to move balloon 44 from the inflated configuration to the uninflated configuration, as discussed herein.

Figure 18:
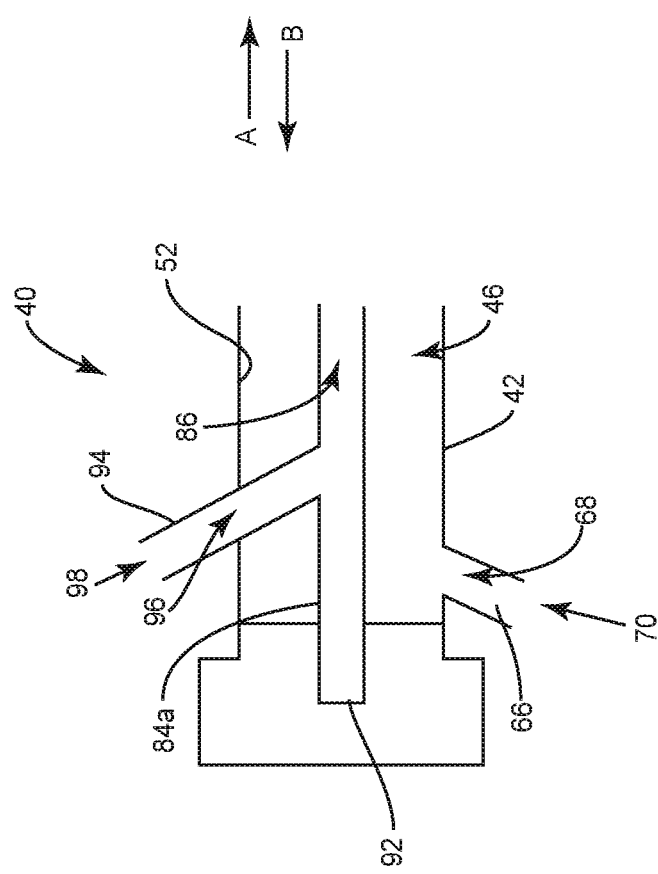
FIG. 18 is a breakaway, side, cross sectional view of a portion of one embodiment of the surgical instrument shown in FIGS. 13 and 13A.

In some embodiments, proximal portion 84a of inner shaft of at least one of balloon catheters 40 shown in FIGS. 13-17 comprises an end wall 92 that defines a proximal limit of lumen 86 and a port 94 having a channel 96 that is in communication with lumen 86, as shown in FIG. 18. Cylindrical portion 42 comprises port 66 that is in communication with passageway 46, as also shown in FIG. 18 and described in greater detail with regard to FIG. 10. In some embodiments, the inflation material may be injected into lumen 86 by positioning an inflation material delivery device, such as, for example, a syringe adjacent to port 94 and ejecting the inflation material from the delivery device such that the inflation material moves through an opening 98 of port 94 and lumen 96 of port 94. The inflation material will then move through lumen 86 of inner shaft 84 in the direction shown by arrow A in FIG. 18 such that the inflation material moves through at least one flow controller 50 positioned within lumen 86. The inflation material will exit lumen 86 via apertures 88 such that the material enters cavity 48 of balloon 44 to move balloon 44 from the uninflated configuration to the inflated configuration. In some embodiments, at least a portion of passageway 46 is filled with the inflation material when balloon 44 is in the inflated configuration.

In some embodiments, the inflation material moves out of cavity 48 of balloon 44 to move balloon 44 from the inflated configuration to the uninflated configuration. This may be done after balloon 44 creates a cavity in bone, for example. It is envisioned that removing balloon catheter 40 from the patient may be easier and/or cause less damage or damage to the patient when balloon 44 is in the uninflated configuration. In some embodiments, balloon 44 is moved from the inflated configuration to the uninflated configuration by coupling a suction device, such as, for example, a syringe and/or vacuum source to port 66 such that suction is created to move the inflation material out of cavity 48 of balloon 44 and through passageway 46 of cylindrical portion 42 in direction B shown in FIG. 18. The inflation material will continue to move in arrow B until the material exits passageway 46 through lumen 68 and opening 70 of port 68 of cylindrical portion 42. In some embodiments, the inflation material will remain within cavity 48 of balloon 44 until suction is applied. That is, balloon 44 will remain in the inflated configuration until suction is applied at port 66 to draw the inflation material through passageway 46 of cylindrical portion 42.

In some embodiments, balloon catheter 40 comprises inner shaft 84 and is configured such that the inflation material moves through passageway 46 of cylindrical portion 42 in a space between inner shaft 84 and cylindrical portion 42 to move balloon 44 between the uninflated and inflated configurations, as discussed herein, Flow controllers 50 are positioned within passageway 46, between the outer surface of inner shaft 84 and inner surface 52 of cylindrical portion 42, as shown in FIGS. 19-30, in order to limit the flow rate of the inflation material as it flows through passageway 46.

In one embodiment, shown in FIGS. 19-20B, balloon catheter 40 comprises one or a plurality of flow controllers 50 that extend continuously from the outer surface of inner shaft 84 to inner surface 52 of cylindrical portion 42. As shown in FIG. 19, flow controllers 50 are spaced apart from one another along central longitudinal axis CLA. However it is envisioned that balloon catheter 40 may comprise a single flow controller 50 that extends continuously from proximal portion 42a of cylindrical portion 42 to distal portion 42b of cylindrical portion 42 and/or from proximal portion 84a of inner shaft 84 to distal portion 84b of inner shaft 84 such that the single flow controller extends the entire length of at least one of cylindrical portion 42 and inner shaft 84.

In the embodiment shown in FIG. 20A, flow controller(s) 50 comprise(s) a plate having one or a plurality of discrete conduits 100 that each extend continuously through and between opposite proximal and distal surfaces 50a, 50b of flow controller(s) 50. In embodiments that comprise a plurality of conduits 100, conduits 100 are nonadjacent to one another or spaced apart such that one conduit 100 is not in communication with another one of conduits 100. In some embodiments, conduits 100 are positioned radially about a circumference of cylindrical portion 42, as shown in FIG. 20A In some embodiments, conduits 100 may have various cross section configurations, such as, for example, oval, oblong, triangular, rectangular, square, polygonal, irregular, uniform, non-uniform, variable, tubular and/or tapered.

In the embodiment shown in FIG. 20B, flow controller(s) comprise(s) a foam material, such as, for example, an open cell foam material or spongiform material/structure comprising a plurality of pores 54, as discussed above with regard to the embodiment shown in FIG. 1B. In some embodiments, at least one of pores 54 extends through proximal and distal surfaces 50a, 50b a respective flow controller 50. In some embodiments, at least one of pores 54 extends through one of proximal and distal surfaces 50a, 50b without extending through the other one of proximal and distal surfaces 50a, 50b. In some embodiments, at least one of pores 54 is in communication with at least another one of pores 54. In some embodiments, pores 54 are interconnected with one another. In some embodiments, pores 54 are nonadjacent to one another, spaced apart and/or are not in communication with one another.

In some embodiments, balloon catheter 40 comprises one or a plurality of flow controllers 50 that are coupled to the outer surface of inner shaft 84, as shown in FIG. 21, for example. In such embodiments, flow controllers 50 may be discrete bands concentric to central longitudinal axis CLA or discrete strips that extend parallel to central longitudinal axis CLA. In some embodiments, flow controller(s) coupled to the outer surface of inner shaft 84 extend continuously from a proximal portion 84a of inner shaft 84 to an opposite distal portion 84b of inner shaft 84. That is, one or more of flow controllers 50 coupled to the outer surface inner shaft 84 may have a maximum length along central longitudinal axis CLA that is equal to a maximum length of inner shaft 84 along central longitudinal axis CLA. In some embodiments, balloon catheter 40 comprises a single flow controller 50 coupled to the outer surface of inner shaft 84 that extends continuously from proximal portion 84a to distal portion 84b and also extends 360 degrees about central longitudinal axis CLA, as shown in FIG. 22, for example. In such embodiments, flow controllers 50 are discrete bands concentric to central longitudinal axis CLA. In some embodiments, balloon catheter 40 comprises a plurality of flow controllers 50 coupled to the outer surface of inner shaft 84 that extend continuously from proximal portion 84a to distal portion 84b and are spaced apart from one another about a circumference of inner shaft 84, as shown in FIG. 23. In such embodiments, flow controllers 50 are discrete strips that extend parallel to central longitudinal axis CLA. In some embodiments, the flow controller(s) 50 coupled to the outer surface of inner shaft 84 that extend(s) continuously from proximal portion 84a to distal portion 84b has/have a uniform height from proximal portion 84a to distal portion 84b. In some embodiments, the flow controller(s) 50 coupled to the outer surface of inner shaft 84 that extend(s) continuously from proximal portion 84a to distal portion 84b taper(s) from proximal portion 84a to distal portion 84b. In some embodiments, the flow controller(s) 50 coupled to the outer surface of inner shaft 84 that extend(s) continuously from proximal portion 84a to distal portion 84b taper(s) from distal portion 84b to proximal portion 84a.

In some embodiments, balloon catheter 40 comprises a plurality of flow controllers 50 coupled to the outer surface of inner shaft 84 that are spaced apart from one another along central longitudinal axis CLA, as shown in FIG. 21. In some embodiments, the spaced apart flow controllers 50 coupled to the outer surface of inner shaft 84 are uniformly spaced apart from one another along central longitudinal axis CLA. In some embodiments, at least one of the spaced apart flow controllers 50 coupled to the outer surface of inner shaft 84 extends 360 degrees about central longitudinal axis CLA, as shown in FIG. 22, for example. In some embodiments, the spaced apart flow controllers 50 coupled to the outer surface of inner shaft 84 are spaced apart from one another along central longitudinal axis CLA, as shown in FIG. 21 and are also spaced apart from one another about a circumference of inner shaft 84, as shown in FIG. 23.

Figure 24:
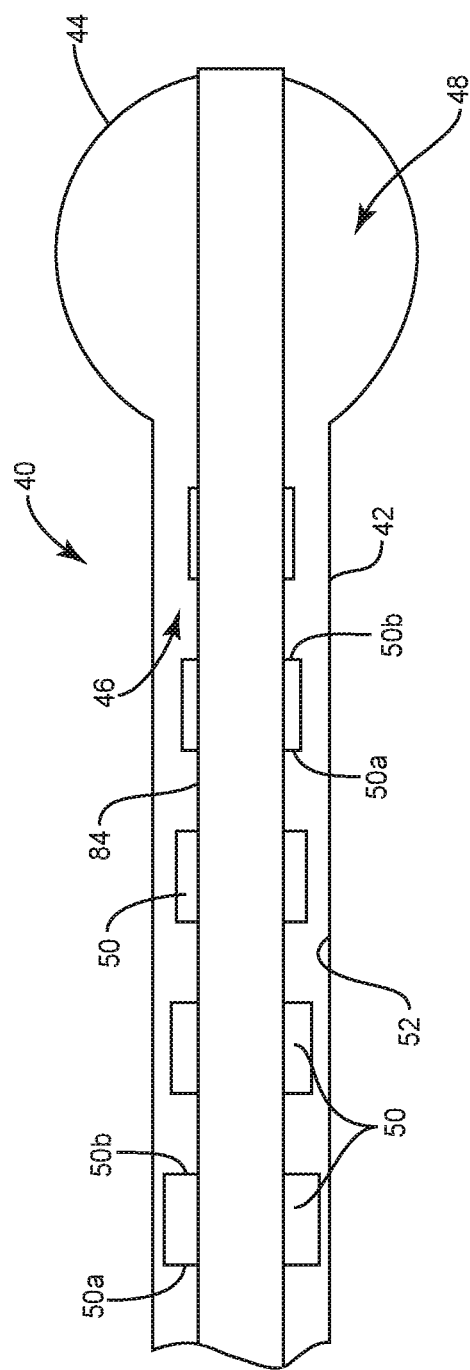
FIG. 24 is a breakaway, side, cross sectional view of one embodiment of the surgical instrument shown in FIG. 23.
Figure 25:
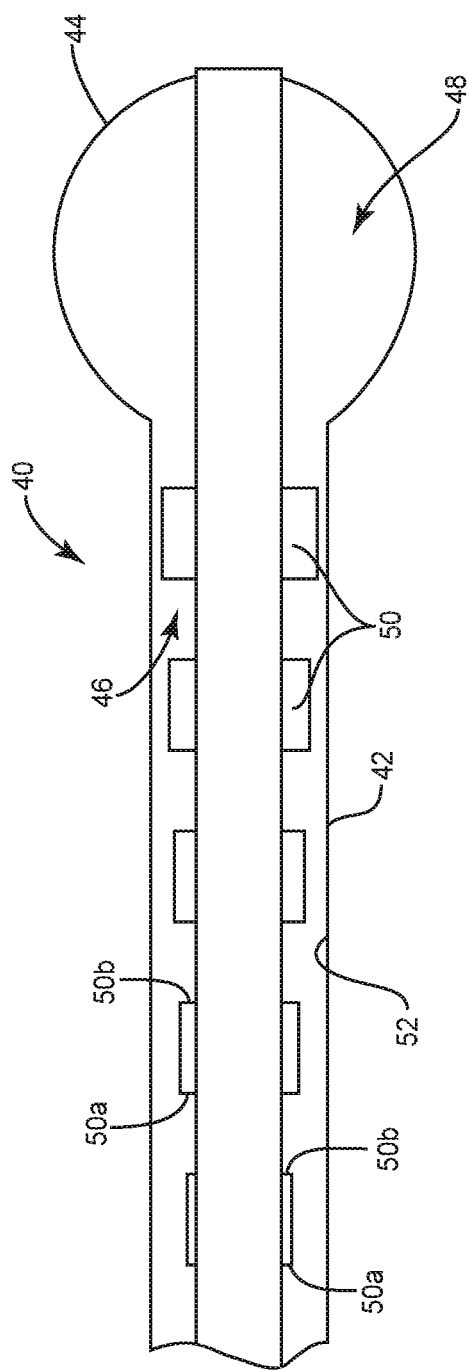
FIG. 25 is a breakaway, side, cross sectional view of one embodiment of the surgical instrument shown in FIG. 23.

In some embodiments, the spaced apart flow controllers 50 coupled to the outer surface of inner shaft 84 are each tapered from proximal portion 50*a* to distal portion 50*b*. In some embodiments, the spaced apart flow controllers 50 coupled to the outer surface of inner shaft 84 are each tapered from distal portion 50*b* to proximal portion 50*a*. In some embodiments, each of the spaced apart flow controllers 50 coupled to the outer surface of inner shaft 84 have the same height, as shown in FIG. 21. In some embodiments, each of the spaced apart flow controllers 50 coupled to the outer surface of inner shaft 84 have a different height, wherein the flow controller 50 having the greatest height is positioned at proximal portion 84*a* of inner shaft 84 and the flow controller 50 having the least height is positioned at distal portion 84*b* of inner shaft, as shown in FIG. 24. In some embodiments, each of the spaced apart flow controllers coupled to the outer surface of inner shaft 84 have a different height, wherein the flow controller 50 having the greatest height is positioned at distal portion 84*b* of inner shaft 84 and the flow controller 50 having the least height is positioned at proximal portion 84*a* of inner shaft 84, as shown in FIG. 25. The height(s) of the flow controller(s) 50 coupled to the outer surface of inner shaft 84 between the flow controllers 50 with the greatest and least heights is less than the height of the flow controller 50 with the greatest height and greater than the flow controller 50 with the least height such that flow controllers 50 have a stepped configuration, as shown in FIGS. 24 and 25.

In some embodiments, balloon catheter 40 comprises one or a plurality of flow controllers 50 positioned in passageway 46 of cylindrical portion 42 between inner shaft 84 and inner surface 52 of cylindrical portion 42 that are coupled to inner surface 52 of cylindrical portion 42 and extend continuously from a proximal portion 42*a* of cylindrical portion 42 to an opposite distal portion 42*b* of cylindrical portion 42. That is, one or more of flow controllers 50 coupled to inner surface 52 of cylindrical portion 42 may have a maximum length along central longitudinal axis CLA that is equal to a maximum length of cylindrical portion 42 along central longitudinal axis CLA. In some embodiments, balloon catheter 40 comprises a single flow controller 50 coupled to inner surface 52 of cylindrical portion 42 that extends continuously from proximal portion 42*a* to distal portion 42*b* and also extends 360 degrees about central longitudinal axis CLA, as shown in FIG. 27, for example. In some embodiments, balloon catheter 40 comprises a plurality of flow controllers 50 coupled to inner surface 52 of cylindrical portion 42 that extend continuously from proximal portion 42*a* to distal portion 42*b* and are spaced apart from one another about a circumference of cylindrical portion 42, as shown in FIG. 28. In some embodiments, the flow controller(s) 50 coupled to inner surface 52 of cylindrical portion 42 that extend(s) continuously from proximal portion 42*a* to distal portion 42*b* has/have a uniform height from proximal portion 42*a* to distal portion 42*b*. In some embodiments, the flow controller(s) 50 coupled to inner surface 52 of cylindrical portion 42 that extend(s) continuously from proximal portion 42*a* to distal portion 42*b* taper(s) from proximal portion 42*a* to distal portion 42*b*. In some embodiments, the flow controller(s) 50 coupled to inner surface 52 of cylindrical portion 42 extend(s) continuously from proximal portion 42*a* to distal portion 42*b* taper(s) from distal portion 42*b* to proximal portion 42*a*.

In some embodiments, balloon catheter 40 comprises a plurality of flow controllers 50 coupled to inner surface 52 of cylindrical portion 42 that are spaced apart from one another along central longitudinal axis CLA, as shown in FIG. 26. In such embodiments, flow controllers 50 may be discrete bands concentric to central longitudinal axis CLA or discrete strips that extend parallel to central longitudinal axis CLA. In some embodiments, the spaced apart flow controllers 50 coupled to inner surface 52 of cylindrical portion 42 are uniformly spaced apart from one another along central longitudinal axis CLA. In some embodiments, at least one of the spaced apart flow controllers 50 coupled to inner surface 52 of cylindrical portion 42 extends 360 degrees about central longitudinal axis CLA, as shown in FIG. 27, for example. In such embodiments, flow controllers 50 are discrete bands concentric to central longitudinal axis CLA. In some embodiments, the spaced apart flow controllers 50 coupled to inner surface 52 of cylindrical portion 42 are spaced apart from one another along central longitudinal axis CLA, as shown in FIG. 26 and are also spaced apart from one another about a circumference of inner shaft 84, as shown in FIG. 28. In such embodiments, flow controllers 50 are discrete strips that extend parallel to central longitudinal axis CLA.

Figure 29:
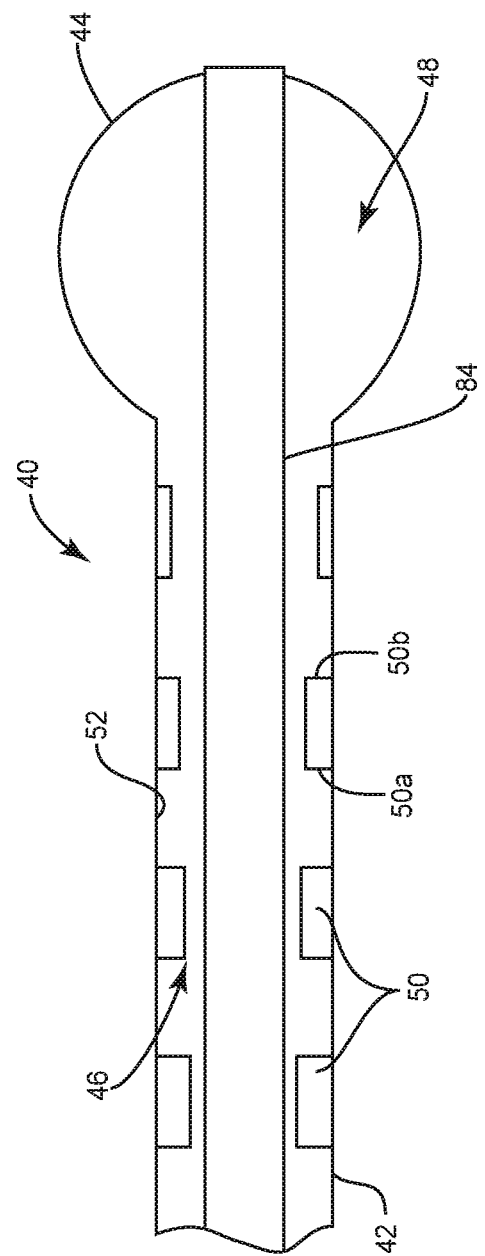
FIG. 29 is a breakaway, side, cross sectional view of one embodiment of the surgical instrument shown in FIG. 26.
Figure 30:
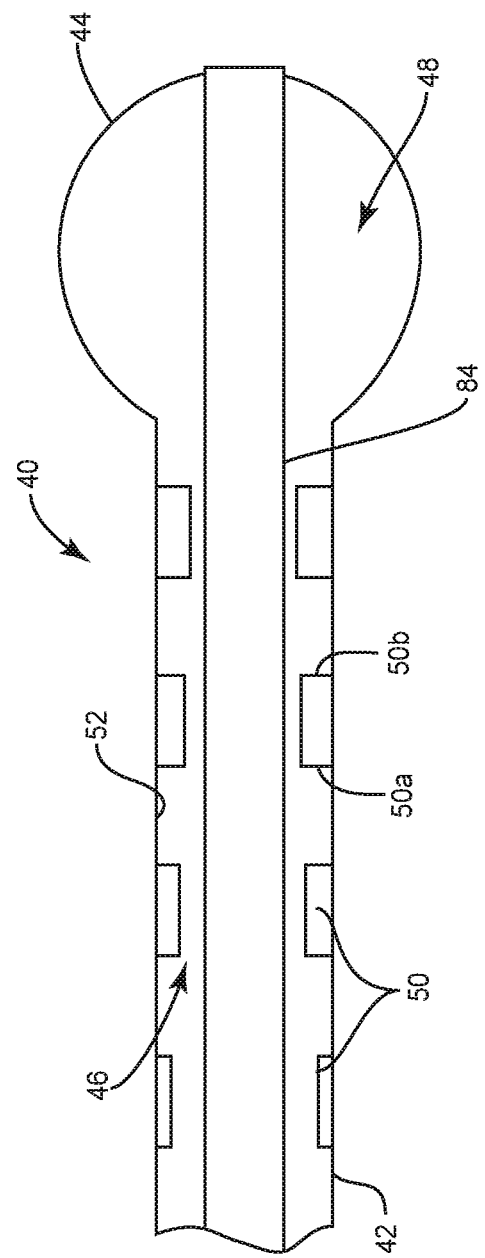
FIG. 30 is a breakaway, side, cross sectional view of one embodiment of the surgical instrument shown in FIG. 26.

In some embodiments, the spaced apart flow controllers 50 coupled to inner surface 52 of cylindrical portion 42 are each tapered from proximal portion 50*a* to distal portion 50*b*. In some embodiments, the spaced apart flow controllers 50 coupled to inner surface 52 of cylindrical portion 42 are each tapered from distal portion 50*b* to proximal portion 50*a*. In some embodiments, each of the spaced apart flow controllers 50 coupled to inner surface 52 of cylindrical portion 42 have the same height, as shown in FIG. 26. In some embodiments, each of the spaced apart flow controllers 50 coupled to inner surface 52 of cylindrical portion 42 have a different height, wherein the flow controller 50 having the greatest height is positioned at proximal portion 42*a* of cylindrical portion 42 and the flow controller 50 having the least height is positioned at distal portion 42*b* of cylindrical portion 42, as shown in FIG. 29. In some embodiments, each of the spaced apart flow controllers 50 inner surface 52 of cylindrical portion 42 have a different height, wherein the flow controller 50 having the greatest height is positioned at distal portion 42*b* of cylindrical portion 42 and the flow controller 50 having the least height is positioned at proximal portion 42*a* of cylindrical portion 42, as shown in FIG. 30. The height(s) of the flow controller(s) 50 coupled to inner surface 52 of cylindrical portion 42 between the flow controllers 50 with the greatest and least heights is less than the height of the flow controller 50 with the greatest height and greater than the flow controller 50 with the least height such that flow controllers 50 have a stepped configuration, as shown in FIGS. 29 and 30.

In use, to treat a bone disorder, such as, for example, a spinal fracture, a medical practitioner obtains access to a target location including at least one vertebra, such as, for example, a fractured vertebra, in any appropriate manner, such as through incision and retraction of tissue. Balloon catheter 40 is moved through the incision and positioned so that balloon 44 is positioned within a vertebral body of the fractured vertebra. In some embodiments, balloon 44 is moved into the vertebral body when balloon 44 is in the uninflated configuration. An inflation material, such as, for example, one of the materials discussed above is moved through passageway 46 and opening 56 such that the material moves into cavity 48 of balloon 44 to move balloon 44 from the uninflated configuration to the inflated configuration. As the material flows through passageway 46, flow controller(s) 50 reduce(s) the rate of flow of the material to prevent balloon 44 from being inflated too quickly. That is, flow controller(s) 50 ensure(s) that balloon 44 is gradually inflated such that balloon 44 pushes cancellous bone of the vertebral body towards cortical walls of the vertebral body to form a cavity within the vertebral body. In some embodiments, the cavity created by balloon 44 is filled with a material, such as, for example, bone cement. In some embodiments, at least a portion of passageway 46 is filled with the inflation material when balloon 44 is in the inflated configuration.

In one embodiment, shown in FIGS. 31 and 32, balloon catheter 40 comprises inner shaft 84 and one or a plurality of flow controllers 50 coupled to outer surface 58 of cylindrical portion 42. In such embodiments, flow controllers 50 are discrete bands concentric to central longitudinal axis CLA. In some embodiments, flow controllers 50 are crimped to outer surface 58. At each position along cylindrical portion 42 to which flow controllers 50 are crimped, the diameter of cylindrical portion 42 decreases. For example, cylindrical portion 42 comprises a first portion that is free of any flow controllers 50 and has an inner diameter d1 and a second portion that comprises at least one flow controller 50 and has an inner diameter d2 that is less than inner diameter d1. In some embodiments, cylindrical portion 42 comprises a third portion that comprises at least one additional flow controller 50 and has an inner diameter d3 that is less than inner diameter d2. In some embodiments, cylindrical portion 42 comprises a fourth portion that comprises at least one additional flow controller 50 and has an inner diameter d4 that is less than inner diameter d3. In some embodiments, each of flow controllers 50 extends 360 degrees about central longitudinal axis CLA, as shown in FIG. 32, for example.

The changes in the inner diameter of cylindrical portion 42 between inner diameter d1, inner diameter d2, inner diameter d3 and inner diameter d4 controls the flow of the inflation material through passageway 46 to gradually inflate balloon 44. In particular, as the inflation material flows through passageway 46, the changes in the inner diameter of cylindrical portion 42 reduce the rate of flow of the material to prevent balloon 40 from being inflated too quickly. That is, the changes in the inner diameter of cylindrical portion 42 ensure that balloon 44 is gradually inflated such that balloon 44 pushes cancellous bone of the vertebral body towards cortical walls of the vertebral body to form a cavity within the vertebral body.

Figure 33:
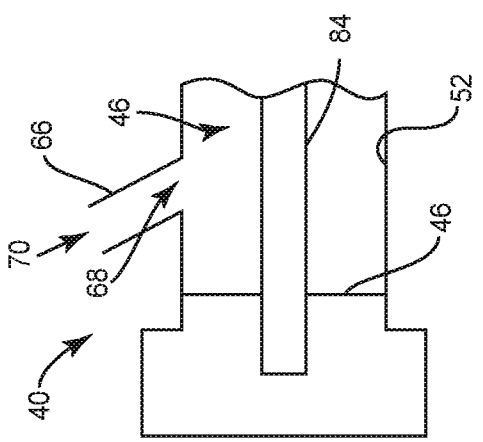
FIG. 33 is a breakaway, side, cross sectional view of a portion of one embodiment of the surgical instruments shown in FIGS. 19, 21, 26 and 31.

In some embodiments, proximal portion 42a of cylindrical portion 42 of at least one of balloon catheters 40 shown in FIGS. 19-32 comprises end wall 64 that defines a proximal limit of passageway 46 and port 66, as described in greater detail with the discussion of the embodiment shown in FIG. 10. As shown in FIG. 33, inner shaft 84 extends through end wall 46. The inflation material may be injected into passageway 46 by positioning an inflation material delivery device, such as, for example, a syringe adjacent to port 66 and ejecting the inflation material from the delivery device such that the inflation material moves through opening 70 of port 66 and lumen 68 of port 66.

Figure 34:
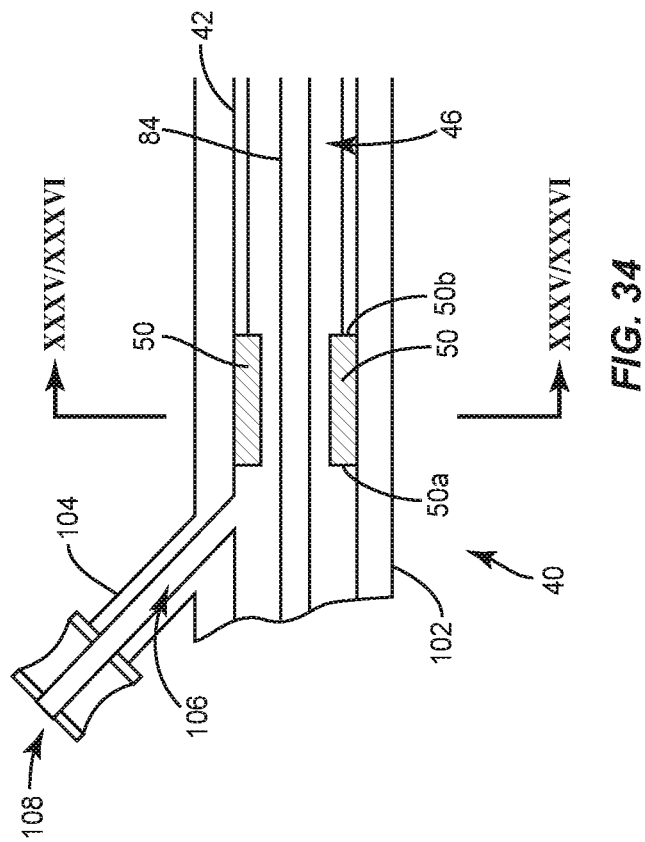
FIG. 34 is a breakaway, side, cross sectional view of a portion of one embodiment of the surgical instruments shown in FIGS. 19, 21 26 and 31.
Figure 36:
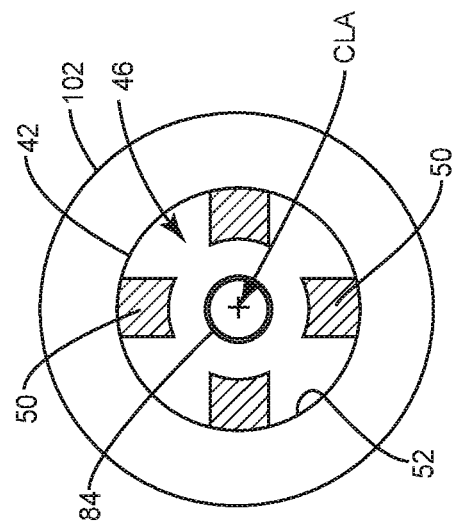
FIG. 36 is a cross sectional view of one embodiment of the portion of one embodiment of components of the surgical instruments shown in FIGS. 19, 21, 26 and 31.
Figure 35:
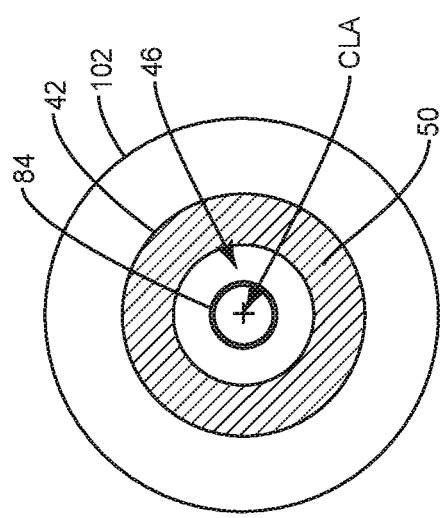
FIG. 35 is a cross sectional view of one embodiment of the portion of one embodiment of components of the surgical instruments shown in FIGS. 19, 21, 26 and 31.

In some embodiments, at least one of balloon catheters 40 shown in FIGS. 19-32 comprises a connector 102 that is positioned about proximal portions 42a, 84a of cylindrical portion 42 and inner shaft 84, as shown in FIG. 34. Connector 102 comprises a port 104 having a lumen 106 that is in communication with passageway 46, as shown in FIG. 34. The inflation material may be injected into passageway 46 by positioning an inflation material delivery device, such as, for example, a syringe adjacent to port 104 and ejecting the inflation material from the delivery device such that the inflation material moves through an opening 108 of port 104 and lumen 106 of port 104. In some embodiments, balloon catheter 40 comprises at least one or a plurality of flow controllers 50 positioned within passageway 46 adjacent to port 104, as shown in FIG. 34. In some embodiments, flow controllers 50 are positioned distal to port 104 such that as an inflation material is ejected from a delivery device and into passageway 46 through port 104, flow controller(s) 50 will limit the rate of flow of the material through passageway 46. In some embodiments, at least one of flow controllers 50 adjacent to port 104 extends 360 degrees about central longitudinal axis CLA, as shown in FIG. 35, for example. In such embodiments, flow controllers 50 are discrete strips that are concentric with central longitudinal axis CLA. In some embodiments, flow controllers 50 adjacent to port 104 are spaced apart from one another about a circumference of cylindrical portion 42, as shown in FIG. 36. In such embodiments, flow controllers 50 are discrete strips that extend parallel to central longitudinal axis CLA.

In some embodiments, a kit containing one or more components of balloon catheter 40 is provided. The kit may comprise components from any of the embodiments discussed herein. In some embodiments, the kit comprises one or more of the inflation materials discussed herein. The kit may also comprise one or more component to assist with inserting balloon catheter 40 into a patient, such as, for example, one or a plurality of cannulas. In some embodiments, the kit comprises a plurality of cannulas having different lengths configured for use with different size patients.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An inflatable bone tamp comprising:
   a first shaft extending along a central longitudinal axis between a first proximal portion and an opposite first distal portion, the first shaft including an inner surface and an outer surface, the inner surface defining a lumen extending therethrough, and the first distal portion including at least one aperture therethrough;
   a second shaft extending between a second proximal portion and an opposite second distal portion, the second shaft including an inner surface, the first shaft being received inside the second shaft, and the outer surface of the first shaft and the inner surface of the second shaft defining a passageway extending through the second shaft;
   an inflatable balloon having an interior, a distal end coupled to the first distal portion of the first shaft and a proximal end coupled to the second distal portion of the second shaft such that a material can flow through the second shaft and into the balloon to inflate the balloon; and a plurality of flow controllers coupled to one of the outer surface of the first shaft and the inner surface of the second shaft inside the passageway that controls the flow of the material through the passageway and into the balloon, each of the plurality of flow controllers protruding into the passageway and being spaced apart from one another about a circumference of a corresponding one of the outer surface of the first shaft and the inner surface of the second shaft, a first of the plurality of flow controllers positioned at a first circumferential position, a second of the plurality of flow controllers positioned at a second circumferential position, a third of the plurality of flow controllers positioned at a third circumferential position, and a fourth of the plurality of flow controllers positioned at a fourth circumferential position, the first circumferential position being adjacent the second circumferential position, the second circumferential position being adjacent the third circumferential position, the third circumferential position being adjacent the fourth circumferential position, and the fourth circumferential position being adjacent the first circumferential position, the first circumferential position being opposite from the third circumferential position, and the second circumferential position being opposite from the fourth circumferential position, each of the plurality of flow controllers including at least a first lateral surface, a second lateral surface, and an inward-facing surface extending between the first lateral surface and the second lateral surface;

wherein the passageway between the first shaft and the second shaft fluidly communicates with the interior of the balloon, and the interior of the balloon fluidly communicates with the lumen of the first shaft through the at least one aperture; and wherein material injected into the passageway moves through the passageway, between the inward-facing surfaces of the plurality of flow controllers and a corresponding opposite one of the outer surface of the first shaft and the inner surface of the second shaft, and between the first lateral surfaces and the second lateral surfaces of adjacent ones of the plurality of flow controllers, and fills the interior of the balloon to facilitate inflation thereof, and the material exits the interior of the balloon through the at least one aperture, and moves through the lumen to facilitate deflation of the balloon.

2. The inflatable bone tamp of claim 1, wherein the first lateral surfaces, the second lateral surfaces, and the inward-facing surfaces of each of the first, the second, the third, and the fourth of the plurality of flow controllers at least in part reside in corresponding planes that are parallel to the central longitudinal axis.

3. The inflatable bone tamp of claim 1, wherein the inward-facing surfaces of the first, the second, the third, and the fourth of the plurality of flow controllers are concave.

4. The inflatable bone tamp of claim 1, further comprising another plurality of flow controllers spaced axially apart from the plurality of flow controllers relative to the central longitudinal axis, each of the another plurality of flow controllers protruding into the passageway and being spaced apart from one another about a circumference of one of the outer surface of the first shaft and the inner surface of the second shaft.

5. The inflatable bone tamp of claim 4, wherein a first of the another plurality of flow controllers positioned at a first circumferential position, a second of the another plurality of flow controllers positioned at a second circumferential position, a third of the another plurality of flow controllers positioned at a third circumferential position, and a fourth of the another plurality of flow controllers positioned at a fourth circumferential position, each of the another plurality of flow controllers including at least a first lateral surface, a second lateral surface, and an inward-facing surface extending between the first lateral surface and the second lateral surface.

6. The inflatable bone tamp of claim 1, wherein each of the plurality of flow controllers is comprised of discrete strips coupled along the one of the outer surface of the first shaft and the inner surface of the second shaft parallel to the central longitudinal axis.

7. The inflatable bone tamp of claim 1, wherein the lumen is tapered from the first proximal portion to a midpoint of the lumen and from the midpoint of the lumen to the first distal portion.

8. The inflatable bone tamp of claim 1, further comprising an end portion connected to the first proximal portion of the first shaft and connected to the second proximal portion of the second shaft, the end portion including a first port communicating with the passageway and a second port communicating with the lumen.

9. The inflatable bone tamp of claim 1, wherein the bone tamp includes a proximal end and an opposite distal end, the balloon being positioned at and adjacent the distal end of the bone tamp, and the plurality of flow controllers being positioned adjacent the proximal end of the bone tamp.

10. The inflatable bone tamp of claim 9, wherein another plurality of flow controllers is positioned adjacent the distal end of the bone tamp.

11. An inflatable bone tamp comprising:
an outer shaft extending along a central longitudinal axis between opposite proximal end and distal end portions, the outer shaft including an inner surface;
an inner shaft positioned within the outer shaft and extending between opposite proximal end and distal end portions, the inner shaft having an inner surface and an outer surface, and the distal end portion of the inner shaft comprising apertures;
a passageway formed between the outer surface of the inner shaft and the inner surface of the outer shaft, and a lumen formed by the inner surface of the inner shaft;
a balloon having a distal end coupled to the distal end portion of the inner shaft and a proximal end coupled to the distal end portion of the outer shaft, the balloon having an interior communicating with the passageway and the lumen, the interior of the balloon communicating with the lumen via the apertures in the distal end portion of the inner shaft; and
a plurality of flow controllers coupled to one of the outer surface of the inner shaft and the inner surface of the outer shaft within the passageway, each of the plurality of flow controllers being spaced apart from one another about a circumference of a corresponding one of the outer surface of the inner shaft and the inner surface of the outer shaft, and each of the plurality of flow controllers protruding into the passageway and including an exposed first side surface, an exposed second side surface, and an exposed inward-facing surface;
wherein a material injected into the passageway moves through the passageway, between the inward-facing surfaces of the plurality of flow controllers and a corresponding opposite one of the outer surface of the inner shaft and the inner surface of the outer shaft, between the exposed first side surfaces and the exposed second side surfaces of adjacent ones of the plurality of flow controllers, and into the interior of the balloon to inflate the balloon; and wherein the material moves out of the balloon, through the apertures, and into the lumen and out of the inner shaft to deflate the balloon.

12. The inflatable bone tamp of claim 11, wherein the bone tamp includes a proximal end and an opposite distal end, the balloon being positioned at and adjacent the distal end of the bone tamp, and the plurality of flow controllers being positioned at least adjacent the proximal end of the bone tamp.

13. The inflatable bone tamp of claim 11, further comprising a first of the plurality of flow controllers positioned at a first circumferential position, a second of the plurality of flow controllers positioned at a second circumferential position, a third of the plurality of flow controllers positioned at a third circumferential position, and a fourth of the plurality of flow controllers positioned at a fourth circumferential position, the first circumferential position being adjacent the second circumferential position, the second circumferential position being adjacent the third circumferential position, the third circumferential position being adjacent the fourth circumferential position, and the fourth circumferential position being adjacent the first circumferential position, the first circumferential position being opposite from the third circumferential position, and the second circumferential position being opposite from the fourth circumferential position.

14. An inflatable bone tamp comprising:

an outer shaft extending along a central longitudinal axis between opposite proximal end and distal end portions, the outer shaft including an inner surface;

an inner shaft positioned within the outer shaft and extending between opposite proximal end and distal end portions, the inner shaft having an inner surface and an outer surface, and the distal end portion of the inner shaft comprising apertures;

a passageway formed between the outer surface of the inner shaft and the inner surface of the outer shaft, and a lumen formed by the inner surface of the inner shaft;

a proximal portion coupled to the shafts such that a first port of the proximal portion is in communication with the passageway and a second port of the proximal portion is in communication with the lumen;

a balloon having a distal end coupled to the distal end portion of the inner shaft and a proximal end coupled to the distal end portion of the outer shaft, the balloon having an interior communicating with the passageway and the lumen, the interior of the balloon communicating with the lumen via the apertures in the distal end portion of the inner shaft; and a plurality of flow controllers coupled to one of the outer surface of the inner shaft and the inner surface of the outer shaft within the passageway, each of the plurality of flow controllers being spaced apart from one another about a circumference of a corresponding one of the outer surface of the inner shaft and the inner surface of the outer shaft, and each of the plurality of flow controllers protruding into the passageway and including an exposed first side surface, an exposed second side surface, and an exposed inward-facing surface;

wherein a material injected into the first port moves through the passageway, between the inward-facing surfaces of the plurality of flow controllers and a corresponding opposite one of the outer surface of the inner shaft and the inner surface of the outer shaft, between the exposed first side surfaces and the exposed second side surfaces of adjacent ones of the plurality of flow controllers, and into the interior of the balloon to inflate the balloon; and wherein the material moves out of the balloon, through the apertures, and into the lumen and out of the second port to deflate the balloon upon suction being applied to the second port.

15. The inflatable bone tamp of claim 14, wherein the bone tamp includes a proximal end and an opposite distal end, the proximal portion being positioned at and adjacent the proximal end of the bone tamp, the balloon being positioned at and adjacent the distal end of the bone tamp, and the plurality of the flow controllers being positioned at least adjacent the proximal portion.

16. The inflatable bone tamp of claim 14, further comprising a first of the plurality of flow controllers positioned at a first circumferential position, a second of the plurality of flow controllers positioned at a second circumferential position, a third of the plurality of flow controllers positioned at a third circumferential position, and a fourth of the plurality of flow controllers positioned at a fourth circumferential position, the first circumferential position being adjacent the second circumferential position, the second circumferential position being adjacent the third circumferential position, the third circumferential position being adjacent the fourth circumferential position, and the fourth circumferential position being adjacent the first circumferential position, the first circumferential position being opposite from the third circumferential position, and the second circumferential position being opposite from the fourth circumferential position.

* * * * *